United States Patent
Mayall et al.

(10) Patent No.: US 10,415,102 B2
(45) Date of Patent: *Sep. 17, 2019

(54) SYSTEM AND METHODS FOR THE DETECTION OF MULTIPLE CHEMICAL COMPOUNDS

(71) Applicant: FredSense Technologies Corp., Calgary (CA)

(72) Inventors: Robert Matthew Mayall, Calgary (CA); Emily Candice Hicks, Calgary (CA); Margaret Mary-Flora Renaud-Young, Calgary (CA); David Christopher Lloyd, Calgary (CA); Lisa Kara Oberding, Calgary (CA); Iain Fraser Scotney George, Calgary (CA)

(73) Assignee: Fredsense Technologies Corp., Calgary, Alberta (CA)

( * ) Notice: Subject to any disclaimer, the term of this patent is extended or adjusted under 35 U.S.C. 154(b) by 158 days.

This patent is subject to a terminal disclaimer.

(21) Appl. No.: 15/613,692

(22) Filed: Jun. 5, 2017

(65) Prior Publication Data

US 2017/0335412 A1 Nov. 23, 2017

Related U.S. Application Data

(63) Continuation of application No. 14/491,367, filed on Sep. 19, 2014, now Pat. No. 9,689,046.

(60) Provisional application No. 61/880,277, filed on Sep. 20, 2013.

(51) Int. Cl.
*C12Q 1/6897* (2018.01)
*C12Q 1/34* (2006.01)

(52) U.S. Cl.
CPC ............. *C12Q 1/6897* (2013.01); *C12Q 1/34* (2013.01); *G01N 2333/938* (2013.01); *G01N 2333/942* (2013.01); *G01N 2458/30* (2013.01)

(58) Field of Classification Search
None
See application file for complete search history.

(56) References Cited

U.S. PATENT DOCUMENTS

| | | | |
|---|---|---|---|
| 5,196,306 | A | 3/1993 | Bobrow et al. |
| 5,409,583 | A | 4/1995 | Yoshioka et al. |
| 6,391,549 | B1 | 5/2002 | Ron et al. |
| 6,750,033 | B2 | 6/2004 | LeJeune et al. |
| 7,041,209 | B1 | 5/2006 | Pizzariello et al. |
| 7,422,892 | B2 | 9/2008 | LeJeune et al. |
| 7,704,745 | B2 | 4/2010 | Baudenbacher et al. |
| 8,702,959 | B2 | 4/2014 | Shacham-Diamand et al. |

FOREIGN PATENT DOCUMENTS

| | | | |
|---|---|---|---|
| WO | 0125472 A1 | 4/2001 | |
| WO | 0169245 A2 | 9/2001 | |

OTHER PUBLICATIONS

Bebeselea, A. et al., "Electrochemical Degradation and Determination of 4-Nitrophenol Using Multiple Pulsed Amperometry at Graphite Based Electrodes", Chem. Bull. "Politehnica" Univ. (Timisoara), vol. 53(67), 1-2, 2008.
Ben-Yoav, H. et al., "A whole cell electrochemical biosensor for water genotoxicity bio-detection", Electrochimica Acta, 2009, 54(25), 6113-6118.
Biran, I. et al., "On-line monitoring of gene expression", Microbiology (Reading, England), 1999, 145 ( Pt 8), 2129-2133.
Da Silva, P.S. et al., "Electrochemical Behavior of Hydroquinone and Catechol at a Silsesquioxane-Modified Carbon Paste Electrode", J. Braz. Chem. Soc., vol. 24, No. 4, 695-699, 2013.
Enache, T. A. & Oliveira-Brett, A. M., "Phenol and Para-Substituted Phenols Electrochemical Oxidation Pathways", Journal of Electroanalytical Chemistry, 2011, 1-35.
Etesami, M. et al., "Electrooxidation of hydroquinone on simply prepared Au—Pt bimetallic nanoparticles", Science China, Chemistry, vol. 56, No. 6, p. 746-754, Jun. 2013.
Funabashi, H. et al., "Electrochemical evaluation of cellular physiological status under stress in *Escherichia coli* with therpoS-lacZ reporter gene", Biotechnology and Bioengineering, vol. 90, No. 4, May 20, 2005.
Hou, P. et al., "Electrochemistry of Hydroquinone Derivatives at Metal and Iodine-modified Metal Electrodes". Chemical Research in Chinese Universities, 2006, 22(4), 493-499.
Huang, W. et al., "Simultaneous determination of 2-nitrophenol and 4-nitrophenol based on the multi-wall carbon nanotubes Nafion-modified electrode". Analytical and Bioanalytical Chemistry, (2003) 375(5), 703-707.
Ko, F. H., & Monbouquette, H. G., Photometric and Electrochemical Enzyme-Multiplied Assay Techniques Using β-Galactosidase as Reporter Enzyme. Biotechnology Progress, 2006, 22(3), 860-865.
Luo, L.-Q. et al., "Derivative voltammetric direct simultaneous determination of nitrophenol isomers at a carbon nanotube modified electrode". Sensors and Actuators B: Chemical, 2008, 135(1), 61-65.
Mathiyarasu, J. et al., "Electrochemical detection of phenol in aqueous solutions", Indian Journal of Chemical Technology, vol. 11, Nov. 2004, p. 797-803.
Nematollahi, D. et al., "Cyclic Voltammetric Study of the Oxidation of Catechols in the Presence of Cyanide Ion", Electroanalysis 2004, 16(16), p. 1359-1365.
Ni, Y. et al., "Simultaneous determination of nitrobenzene and nitro-substituted phenols by differential pulse voltammetry and chemometrics". Analytica Chimica Acta 431 (2001), 101-113.
Sripriya, R. et al., "Voltammetric analysis of hydroquinone, ascorbic acid, nitrobenzene and benzyl chloride in aqueous, non-aqueous, micellar and microemulsion media". Colloid and Polymer Science (2006) 285(1), 39-48.

(Continued)

*Primary Examiner* — Suzanne M Noakes
*Assistant Examiner* — Jae W Lee
(74) *Attorney, Agent, or Firm* — Bereskin & Parr LLP/S.E.N.C.R.L., s.r.l.; Micheline Gravelle

(57) ABSTRACT

Methods that may be used for the electrochemical detection of multiple parameters, including chemical compounds. Further provided are cells that may be used in the electrochemical detection of multiple parameters, including chemical compounds, as well as a kit for the electrochemical detection of multiple parameters, including chemical compounds.

10 Claims, 13 Drawing Sheets

Specification includes a Sequence Listing.

(56) References Cited

OTHER PUBLICATIONS

Togo, C. A. et al., "Novel detection of *Escherichia coli* β-d-glucuronidase activity using a microbially-modified glassy carbon electrode and its potential for faecal pollution monitoring". Biotechnology Letters, (2007) 29(4), 531-537.
Tomasic, J. and D. Keglevic, "The Kinetics of Hydrolysis of Synthetic Glucuronic Esters and Glucuronic Ethers by Bovine Liver and *Escherichia coli* β-Glucuronidase", Biochem. J. (1973) 133, 789-795.
Vijayan, M. & Krishnan, V. (1995). "Electrocatalytic oxidation of hydroquinone on a polypyrrole-coated glassy carbon electrode". Electroanalysis, 1995, 7(2), 197-198.
Yang, Y-L. et al., "Amperometric Determination of 4-Nitrophenol at Multi-Walled Carbon Nanotube-Poly (Diphenylamine) Composite Modified Glassy Carbon Electrode", Int. J. Electrochem. Sci. 6 (2011) 3902-3912.
Yoshimura, F. and H. Nikaido, "Permeability of Pseudomonas aeruginosa outer membrane to hydrophilic solutes", Journal of Bacteriology, J. Bacteriology, vol. 152, 1982, p. 636-642.

SYSTEM AND METHODS FOR THE DETECTION OF MULTIPLE CHEMICAL COMPOUNDS

RELATED APPLICATIONS

This application is a continuation of U.S. application Ser. No. 14/491,367 (now allowed), which claims benefit of 35 U.S.C. 119 based on priority of U.S. Provisional Patent Application No. 61/880,277 filed on Sep. 20, 2013, both of which are incorporated herein in their entirety.

INCORPORATION OF SEQUENCE LISTING

A computer readable form of the Sequence Listing "21806-P44849US02_SequenceListing.txt" (36,864 bytes), submitted via EFS-WEB and amended on Jun. 26, 2017, is herein incorporated by reference.

FIELD OF THE DISCLOSURE

The present disclosure relates to methods for the detection of chemical compounds. More particularly, the present disclosure relates to methods for detecting chemical compounds using electrochemical means.

BACKGROUND OF THE DISCLOSURE

The following paragraphs are provided by way of background to the present disclosure. They are not however an admission that anything discussed therein is prior art or part of the knowledge of persons skilled in the art.

The reliable and rapid detection of chemical compounds in a liquid medium is desirable in many industrial processes, and detection methodologies uniquely relating a chemical property of a compound requiring detection to a detectable output signal are manifold. Recently, methods involving the use of reporter genes have been developed to detect the presence of chemical compounds. For example, the method disclosed in U.S. Pat. No. 6,391,549 permits the detection of a chemical compound using an electrochemical cell and a reporter polypeptide mediating the production of an electrically active compound. The method may be used to assay a single sample, or alternatively multiple samples may be assayed simultaneously. However the method is impractical where multiple chemical compounds require detection. In particular, in order to detect multiple chemical compounds, in accordance with the specification of U.S. Pat. No. 6,391,549, an electrical cell would be inserted in a first sample to detect a chemical compound, an assay result would be obtained, and then the electrical cell would be removed from the sample, cleaned and recalibrated for assaying for a second and any subsequent chemical compounds. Alternatively, two or more electrical cells are used in order to detect two or more chemical compounds. Thus, one of the drawbacks of the methods disclosed by U.S. Pat. No. 6,391,549, is that in order to detect the presence of multiple chemical compounds in an assay sample, it is required that either multiple assay samples are available, and, furthermore, that multiple electrochemical cells are employed, or that multiple non-simultaneous measurements are conducted. The former requires the presence of sufficient assay sample, and, moreover, requires a complex and impractical electrical component, in particular where a substantial number of different chemical compounds require detection. The latter is a time consuming methodology, and potentially more prone to operator error.

The reporter gene based methodologies for the detection of chemical compounds known to the prior art, including those provided by U.S. Pat. No. 6,391,549, are unsuitable for use in instances where it is desirable that multiple chemical compounds are detected in an assay sample. There exists therefore in the art a need for improved methods for the detection of chemical compounds.

SUMMARY OF THE DISCLOSURE

The following paragraphs are intended to introduce the reader to the more detailed description that follows and not to define or limited the claimed subject matter of the present disclosure.

The present disclosure relates to methods for the detection of multiple parameters in a liquid medium. Accordingly, the present disclosure provides, in at least one aspect, at least one embodiment of a method for simultaneously detecting two parameters in a liquid medium comprising:
(i) providing a liquid medium comprising a first and second parameter;
(ii) contacting in a vessel the liquid medium with cells and a first and second substrate to form an assay mixture, wherein the first substrate comprises a first electroactive analyte chemically linked to a first carrier and the second substrate comprises a second electroactive analyte chemically linked to a second carrier; and wherein the cells comprise a chimeric nucleic acid construct comprising in the 5' to 3' direction of translation as operably linked components a first nucleic acid construct comprising:
(a) a first promoter inducible by the first parameter; and
(b) a nucleic acid sequence encoding a first reporter polypeptide comprising a first hydrolase capable of hydrolyzing the first substrate and releasing the first electroactive analyte from the carrier; and
a second nucleic acid construct comprising:
(c) a second promoter inducible by the second parameter; and
(d) a nucleic acid sequence encoding a second polypeptide comprising a second hydrolase capable of hydrolyzing the second substrate and releasing the second electroactive analyte from the carrier;
(iii) detecting an electrical signal facilitated by the first and second electroactive analyte in the assay mixture, wherein detecting the electrical signal facilitated by the first and second electroactive analyte detects the first and second parameters in the liquid medium.

In another aspect, the present disclosure provides a cell comprising a chimeric nucleic acid sequence comprising in the 5' to 3' direction of translation as operably linked components a first nucleic acid construct comprising:
(a) a first promoter operable in the cell; and
(b) a nucleic acid sequence encoding a first reporter polypeptide comprising a first hydrolase capable of hydrolyzing a first substrate comprising a first electroactive analyte and a first carrier to release the first electroactive analyte from the carrier; and
a second nucleic acid construct comprising:
(c) a second promoter operable in the cell; and
(d) a nucleic acid sequence encoding a second reporter polypeptide comprising a second hydrolase capable of hydrolyzing a second substrate comprising a second electroactive analyte and a second carrier to release the second electroactive analyte from the carrier.

In a preferred embodiment, the first promoter is an inducible promoter. In a further preferred embodiment, the first and the second promoter are inducible promoters.

In yet a further aspect, the present disclosure provides a mixture comprising two cells, the first cell comprising a first chimeric nucleic acid sequence comprising in the 5' to 3' direction of translation as operably linked components a first nucleic acid construct comprising:
  (a) a first promoter operable in the first cell; and
  (b) a nucleic acid sequence encoding a first reporter polypeptide comprising a first hydrolase capable of hydrolyzing a first substrate comprising a first electroactive analyte and a first carrier to release the first electroactive analyte from the carrier; and the second cell comprising a second chimeric nucleic acid sequence comprising in the 5' to 3' direction of translation as operably linked components a first nucleic acid construct comprising:
  (c) a second promoter operable in the second cell; and
  (d) a nucleic acid sequence encoding a second reporter polypeptide comprising a second hydrolase capable of hydrolyzing a second substrate comprising a second electroactive analyte and a second carrier to release the second electroactive analyte from the carrier.

In yet a further aspect, the present disclosure relates to a method of detecting a first and second electroactive analyte in a liquid medium, the method comprising:
  (i) contacting in a vessel the liquid medium and (a) a first substrate comprising a first electroactive analyte chemically linked to a first carrier; (b) a second substrate comprising a second electroactive analyte chemically linked to a second carrier; (c) a first reporter polypeptide comprising a first hydrolase; and (d) a second reporter polypeptide comprising a second hydrolase, to form an assay mixture, wherein the first hydrolase is capable of hydrolyzing the first substrate and the second hydrolase is capable of hydrolyzing the second substrate to release the first and second substrate from the first and second carrier; and
  (ii) detecting an electrical signal facilitated by the first and second electroactive analyte in the assay mixture, wherein detecting the electrical signal facilitated by the first and second electroactive analyte detects the first and second parameters in the liquid medium.

In yet another aspect, the present disclosure also relates to a diagnostic kit and provides at least one embodiment of a diagnostic kit for simultaneously detecting two parameters comprising:
  (i) a cell comprising a chimeric nucleic acid sequence comprising in the 5' to 3' direction of translation as operably linked components a first nucleic acid construct comprising:
    (a) a first promoter operable in the cell; and
    (b) a nucleic acid sequence encoding a first reporter polypeptide comprising a first hydrolase capable of hydrolyzing a first substrate comprising a first electroactive analyte and a first carrier and releasing the first electroactive analyte from the carrier; and
  a second nucleic acid construct comprising:
    (c) a second promoter operable in the cell; and
    (d) a nucleic acid sequence encoding a second reporter polypeptide comprising a second hydrolase capable of hydrolyzing a second substrate comprising a second electroactive analyte and a second carrier and releasing the second electroactive analyte from the carrier;

(ii) a first and second substrate; and
  (iii) instructions for use or storage of the kit.

Other features and advantages of the present disclosure will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description

BRIEF DESCRIPTION OF THE DRAWINGS

The disclosure is in the hereinafter provided paragraphs described in relation to its Figures. The Figures provided herein are provided for illustration purposes and are not intended to limit the present disclosure.

DETAILED DESCRIPTION OF THE DISCLOSURE

Figure 1:
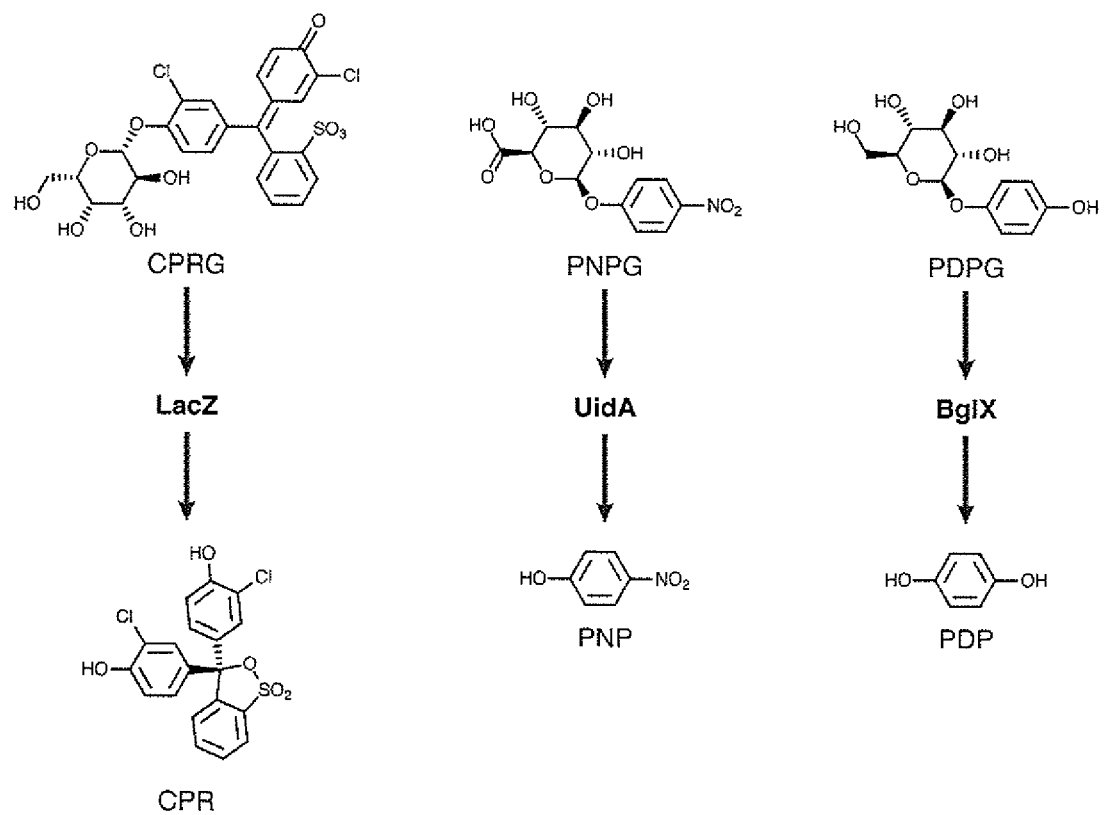
FIG. 1 depicts the chemical formulas of certain substrates and conversion thereof into electroactive analytes, notably the conversion of chlorophenol red-β-D galactopyranoside (CPRG) to chlorophenol red (CPR), para-nitrophenol-β-D-glucuronide (PNPG) to para-nitrophenol (PNP), para-diphenol-β-D-glucopyranoside (PDPG) to para-dihydroxyphenol (PDP).

Various compositions or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions or processes having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicants, inventors or owners do not intend to abandon, disclaim or dedicate to the public any such subject matter by its disclosure in this document.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

All patents and patent applications, and other publications, cited herein, whether supra or infra, including nucleic acid and polypeptide sequences from GenBank, SwissPro and other databases, are hereby incorporated by reference in their entirety, where permitted.

It is further noted that, as used in this specification and the appended claims, the singular forms "a", "an", and "the" include plural referents unless the context clearly dictates otherwise.

As hereinbefore mentioned, the present disclosure relates to methods for detecting multiple parameters in a liquid sample. The herein provided methods represent a novel and efficient means for detecting multiple parameters, including the presence of multiple chemical compounds. The methods of the present disclosure are particularly advantageous in that they permit the simultaneous detection of two or more compounds in a single vessel using a single electrical cell. To the best of the inventors' knowledge, the present disclosure provides, for the first time, a methodology involving the use of multiple reporter genes capable of facilitating the generation of separate electrical signals in response to the presence of two or more parameters in a single vessel using a single electrical cell. Thus a limited amount of assay sample is required in order to conduct the assay, and the electrical signal detection component of the assay is straightforward and inexpensive to manufacture and operate. Furthermore the source assay materials required for the assays are inexpensive and readily available, rendering the assays useful for implementation in a wide range of commercial applications.

Accordingly, the present disclosure provides, in at least one aspect, at least one embodiment of a method for simultaneously detecting two parameters in a liquid medium comprising:

(i) providing a liquid medium comprising a first and second parameter;

(ii) contacting in a vessel the liquid medium with cells and a first and second substrate to form an assay mixture, wherein the first substrate comprises a first electroactive analyte chemically linked to a first carrier and the second substrate comprises a second electroactive analyte chemically linked to a second carrier; and wherein the cells comprise a chimeric nucleic acid construct comprising in the 5' to 3' direction of translation as operably linked components a first nucleic acid construct comprising:

(a) a first promoter inducible by the first parameter; and (b) a nucleic acid sequence encoding a first reporter polypeptide comprising a first hydrolase capable of hydrolyzing the first substrate and releasing the first electroactive analyte from the carrier; and a second nucleic acid construct comprising:

(c) a second promoter inducible by the second parameter; and (d) a nucleic acid sequence encoding a second reporter polypeptide comprising a second hydrolase capable of hydrolyzing the second substrate and releasing second electroactive analyte from the carrier;

(iii) detecting an electrical signal facilitated by the first and second electroactive analyte in the assay mixture, wherein detecting the electrical signal facilitated by the first and second electroactive analyte detects the first and second parameters in the liquid medium.

Definitions

Unless defined otherwise, all technical and scientific terms used herein have the same meaning as commonly understood by one of ordinary skill in the art to which the disclosure pertains.

The term "carrier" as used herein refers to a compound which can be chemically linked to an electroactive analyte and when linked thereto can be hydrolyzed, e.g. by a hydrolase, to form upon hydrolysis an electroactive analyte and the carrier.

The term "electroactive analyte" as used herein refers to a compound capable of being reduced and/or oxidized when a voltage is applied to an electrical cell and facilitate an electrical current in such electrochemical cell.

The term "hydrolase" as used herein refers to any and all enzymes comprising a sequence of amino acid residues which is (i) substantially identical to the amino acid sequences constituting any hydrolase polypeptide set fort herein, including, for example, SEQ.ID NO:2, SEQ. ID NO:4, SEQ.ID NO:6, or (ii) encoded by a nucleic acid sequence capable of hybridizing under at least moderately stringent conditions to any nucleic acid sequence encoding any hydrolase polypeptide set forth herein, but for the use of synonymous codons.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil, and xanthine and hypoxanthine.

The herein interchangeably used terms "nucleic acid sequence encoding a hydrolase" and "nucleic acid sequence encoding a hydrolase polypeptide", refer to any and all nucleic acid sequences encoding a hydrolase polypeptide, including, for example, SEQ.ID NO:1, SEQ.ID NO:3 and SEQ.ID NO:5. Nucleic acid sequences encoding a hydrolase polypeptide further include any and all nucleic acid sequences which (i) encode polypeptides that are substantially identical to the hydrolase polypeptide sequences set forth herein; or (ii) hybridize to any hydrolase nucleic acid sequences set forth herein under at least moderately stringent hybridization conditions or which would hybridize thereto under at least moderately stringent conditions but for the use of synonymous codons.

By the term "substantially identical" it is meant that two polypeptide sequences preferably are at least 70% identical, and more preferably are at least 85% identical and most preferably at least 95% identical, for example 96%, 97%, 98% or 99% identical. In order to determine the percentage of identity between two polypeptide sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, j G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/0.1% SOS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "chimeric" as used herein in the context of nucleic acid sequences refers to at least two linked nucleic acid sequences which are not naturally linked. Chimeric nucleic acid sequences include linked nucleic acid sequences of different natural origins. For example a nucleic acid sequence constituting a bacterial promoter linked to a nucleic acid sequence encoding a non-bacterial hydrolase protein is considered chimeric. Chimeric nucleic acid sequences also may comprise nucleic acid sequences of the same natural origin, provided they are not naturally linked. For example a nucleic acid sequence constituting a promoter obtained from a particular cell-type may be linked to a nucleic acid sequence encoding a polypeptide obtained from that same cell-type, but not normally linked to the nucleic acid sequence constituting the promoter, Chimeric nucleic acid sequences also include nucleic acid sequences comprising any naturally occurring nucleic acid sequence linked to any non-naturally occurring nucleic acid sequence.

The term "promoter" as used herein means any nucleic acid sequence element capable of conferring, effecting, initiating, directing, or enhancing transcription of a nucleic acid sequence element operably linked to the promoter, including, without limitation, SEQ.ID NO:7, SEQ.ID NO:8, SEQ.ID NO:9, SEQ.ID NO:10, SEQ.ID NO:11, SEQ.ID NO:12, SEQ.ID NO:13, SEQ.ID NO:14, SEQ.ID NO:15, SEQ.ID NO:16, SEQ.ID NO:17, SEQ.ID NO:18, and SEQ.ID NO:19. A promoter is generally located 5' (i.e. upstream) of the transcribed nucleic acid sequence element. The transcribed nucleic acid sequence, in accordance herewith, corresponds with a coding region, and transcription thereof, in accordance herewith, effects the production of a polypeptide.

The terms "inducible promoter" or "promoter inducible by a parameter", as may be used interchangeably herein, refer to a promoter which is activated by the presence of an exogenous stimulus, e.g. the presence of an exogenous parameter.

The term "constitutive promoter" as used herein refers to a promoter which provides transcription at a relatively constant rate independent from exogenous stimuli.

The term "reporter polypeptide" as used herein is a polypeptide that is used in order to mediate detection of a parameter.

The term "parameter" refers to the detectable existence of a condition in a liquid medium, including, without limitation, temperature, light, or the presence of a chemical compound.

General Implementation

In accordance with at least one embodiment of the present disclosure, one aspect of the methods herein provided involves contacting, preferably by mixing, in a liquid medium comprising two parameters, a first and second substrate, the first substrate comprising a first carrier and a first electroactive analyte, and the second substrate comprising a second carrier and a second electroactive analyte. The electroactive analyte in accordance herewith is a chemical compound which when free in a solution to which a voltage is applied, is capable of generating an electrical signal. Moreover when an electroactive analyte is chemically linked to the carrier and in solution, the application of a voltage to the solution does not generate a substantive electrical signal. In accordance herewith, the first and second electroactive analytes are non-identical chemical compounds. In further particularly preferred embodiments, the first and second electroactive analytes are selected such that they have distinct redox properties. By the term "distinct redox properties" it is meant that when a voltage is applied to the assay mixture in order to detect the electroactive analytes, as hereinafter described, such voltage application results in the generation of an electrical current through reduction and/or oxidation of the first and second electroactive analyte at voltages sufficiently separate from each other so that the amperage generated by the first electroactive analyte can be detected without substantive interference by the amperage generated by the second electroactive analyte. Thus the difference in voltage at which the first and second electroactive analyte provide an amperage is at least from about 0.1 Volt to about 0.5 Volt, more preferably at about 0.25 Volt to about 0.5 Volt, and in certain preferred embodiments, the difference in voltage at which the first and second electroactive analyte provide an amperage may be as low as 10 mV, e.g. between 0.01 V and 0.02 V. Electroactive analytes are further selected in such a manner that they do not damage or react chemically with the electrode that is used. Suitable electroactive analytes that may be used in accordance with the present disclosure are any electroactive analytes having a voltage range of approximately within +/−2 Volt when in an aqueous solution. Suitable electroactive analytes include independently selected phenolic compounds; single, double or triple ring aromatic compounds; phosphate conjugated compounds; chlorine or bromine substituted compounds; ring compounds comprising a double bond; indole-based compounds, cyanide based compounds; metal compounds; metal-conjugated organics (e.g. ferrocene); compounds with oxidizable alcohol groups; substituted naphthalene compounds; hydrazide based compounds, including 2-[4-(methylthio)phenyl]acetohydrazide; and triazole compounds and their derivatives, including -(4-methyltiobenzyl)-1,2,4-triazole-5-thione; and aromatic nitro compounds, such as para-nitrophenol (also known as 4-nitrophenol) (PNP). Further specific suitable electroactive analytes include, without limitation, para-diphenol (also known as 1,4-diphenol and as hydroquinone) (PDP), ortho-nitrophenol (ONP), 5-bromo-4-chloro-β-indolyl-β-D-galactopyranoside (X-GAL), chlorophenol-red (also known as 2-chloro-4-[3-chloro-4-hydroxyphenyl)-1,1-dioxobenzo[c]oxathiol-3-yl]phenol (CPR) bicarbazolyl), para-aminophenol (PAP), diazapam, ferrocyanide, nitrazepam, and papaverine. In preferred embodiments of the present disclosure, the electroactive analytes PNP, PDP, PAP and CPR are used.

The first and second carrier as used herein are chemical compounds which when chemically linked to an electroactive analyte are capable of being enzymatically hydrolyzed by a hydrolase. The first and second carrier selected may be chemically identical or may be chemically distinct. Suitable carriers that may be used in accordance herewith are any independently selected compounds that can function as a carrier, including any sugars and derivatives thereof. In preferred embodiments, the sugars used are glucose or a derivative thereof, including any oligosaccharide glucose linked to another molecule, phospho-glucose, any glucose-6-phosphate, glucose molecule modified with phosphate, nitrate, or any other chemical group, or galactose or a derivative thereof, including polygalactose, xylose, ribose, fructose, maltose, sucrose, chitin, any modified version of these chemicals, any disaccharide, any oligosaccharide, any orientation of these sugars D or L, any ketoses, aldose, any furanose or pyranose sugar type of any of the aforementioned sugars. Further carriers that may be used are glyceraldehyde, erythrose, threose, arabinose, lyxose, allose, altrose, mannose, gulose, idose, and talose. In particularly preferred embodiments, the carriers used in accordance herewith are β-glucopyranoside, β-galactopyranoside and β-D-glucoronide. Further carriers that may be used are mannoses and derivatives thereof; fructoses and derivatives thereof; fucoses and derivatives thereof; xyloses and derivatives thereof; rhamnoses and derivatives thereof; and chitin and derivatives thereof. Sugar linkages may be any beta- or alpha-linkage, including beta-1-4, beta-1-6, alpha-1-4 and alpha-1-6.

As hereinbefore mentioned, in accordance herewith the first and second carrier and first and second electroactive analyte are chemically linked to form a first and second substrate. Preferred substrates used in accordance herewith are chlorophenol red-β-D-galactopyranoside (CPRG), para-nitrophenol-β-D-glucuronide (PNPG), para-di-phenol-β-D-glucopyranoside (also known as arbutin) (PDPG) and para-aminophenol-β-galactopyranoside (PAPG). The substrate may be added in any form to the liquid medium, for example in the form of a pure or substantially pure compound. In another embodiment, the substrate is produced by the cells of the present disclosure, for example by including in the chimeric nucleic acid sequence, one or more sequences encoding polypeptides capable of mediating the production of the substrate in the cells. In a further embodiment in accordance herewith, a first cell produces the substrate, and a second cell produces the hydrolase.

In accordance herewith, the liquid medium is further mixed with a first reporter polypeptide comprising a first hydrolase and second reporter polypeptide comprising a second hydrolase, wherein the first hydrolase is capable of hydrolyzing the first substrate and the second hydrolase is capable of hydrolyzing the second substrate. It is preferable that the hydrolases are independently selected in such a manner that the first hydrolase and the second hydrolase are specific for hydrolysis of the first and second substrate, respectively. With term "specific" it is meant that hydrolyis by the first hydrolase of the second substrate is less than 5% (w/w), more preferably less than 1% (w/w) and most preferably 0.1% or less, and that the hydrolysis by the second hydrolase of the first substrate is less than 5% (w/w), more preferably less than 1% (w/w) and most preferably 0.1% or less. Preferred hydrolases are polypeptides capable of hydrolyzing the substrates CPRG, PNPG, PAPG and PDPG. Thus in preferred embodiments, the hydrolases are selected from a β-galactosidase, a β-D-glucuronidase and a β-D-glucosidase, and more preferably the hydrolases selected from the β-galactosidase having SEQ.ID. NO:2, the β-D-glucoronidase having SEQ.ID. NO:4 and the β-D-glucosidase, having SEQ.ID NO:6. As illustrated in FIG. 1, the hydrolases β-galactosidase having SEQ.ID. NO:2, β-D-glucuronidase having SEQ.ID. NO:4 and β-D-glucosidase, having SEQ.ID NO:6. are capable of hydrolyzing CPRG, PNPG and PDGP, respectively. The first and second reporter polypeptide, in addition to a first and second hydrolase polypeptide, may comprise additional peptide sequence, for example, a detection tag sequence, or the first and second reporter polypeptide may be restricted to and consist of the first and second hydrolase.

Further hydrolases that may be used in accordance herewith include: agarases including α-agarase, and β-agarase; amylases including α-amylase, β-amylase, and isoamylase; arabinosidases including β-L-arabinosidase, and arabinan endo-1,5-α-L-arabinosidase; facto-N-biosidase; carageenases including t-carrageenase, κ-carrageenase, and λ-carrageenase; cellulases; cellobiosidases including, cellulose 1,4-β-cellobiosidase (non-reducing end), and cellulose 1,4-β-cellobiosidase (reducing end); ceramidases, including glucosulceramidase, galactosylceramidase galactosylgalactoyslglucosylceramidase, glycosylceramidase, and endoglycosylceramidase; chitinases; chitosanase; dextrinases, including cyclomaltodextrinase, mycodextranase, and limit dextrinase; epimerases including UDP-N-acetylglucosamine 2-epimerase, and UDP-N,N'-diacetylbacillosamine 2-epimerase; fructofuranosidases, including β-fructofuranosidase; fucosidases, including β-D-fucosidase, α-L-fucosidase, 1,2-α-L-fucosidase, 1,3-α-L-fucosidase, and 1,6-α-L-fucosidase; fructosidases, including fructan β-fructosidase, fructan β-(2,1)-fructosidase, and fructan β-(2,6)-fructosidase; furanosidases, including non-reducing end α-L-arabinofuranosidase, and β-galactofuranosidase, non-reducing end β-L-arabinofuranosidase; galactosaminidase, including α-acetyl-galactosamindase, β-acetyl-galactoseaminidase, endo-α-N-acetylgalactosaminidase, and endogalactosaminidase; galactanases, including arabinogalactan endo-β-1,4-galactanase, and galactan endo-β-1,3-galactanase; galactosidases, including α-galactosidase, β-galactosidase, 6-phospho-β-galactosidase, capsular-polysaccharide endo-1,3-α-galactosidase, blood-group-substance endo-1,4-β-galactosidase, keratan-sulfate endo-1, 4-β-galactosidase, galactan endo-1,6-β-galactosidase, galactan 1,3-β-galactosidase, blood group B linear chain α-1,3-galactosidase, and blood group B branched chain α-1,3-galactosidase; galacturonases, including polygalacturonase; galacturonidases, including galacturan 1,4-α-galacturonidase, and exo-poly-α-galacturonidase; protein O-GlcNAcase; glucanases, including endo-1,3(4)-β-glucanase, xyloglucan-specific endo-β-1,4-glucanase, and xyloglucan-specific exo-β-1,4-glucanase; glucosaminidases, including hyaluronglucosaminidase, α-N-acetyl-glucosamindase, Mannosyl-glycoprotein endo-β-N-acetylglucosaminidase, and exo-1,4-β-D-glucosaminidase, β-aspartyl-N-acetylglucosaminidase; glucosidases, including 1,4-α-glucosidase, oligo-1,6-gludosidase, α-glucosidase, β-glucosidase, amylo-α-1,6-glucosidase, glucan-endo-1,3-β-glucosidase, GDP-glucosidase, sucrose-α-glucosidase, glucan 1,3-β-glucosidase, glucan endo-1,3-α-glucosidase, glucan 1,6-α-glucosidase, glucan endo-1,2-β-glucosidase, Glucan 1,4-β-glucosidase, glucan endo-1,6-(i-glucosidase, glucan 1,3-α-glucosidase, 6-phospho-3-glucosidase, steryl-β-glucosidase, 3-α-M-strictosidine β-glucosidase, mannosyl-oligosaccharide glucosidase, protein-glucosylgalactosylhydroxylysine glucosidase, 2-deoxyglucosidase, branched-dextran exo-1,2-α-glucosidase, amygdalin β-glucosidase, prunasin β-glucosidase, vicianin β-glucosidase, oligoxyloglucan β-glycosidase, maltose-6'-phosphate glucosidase, raucaffricine β-glucosidase, coniferin β-glucosidase, thioglucosidase; 4-hydroxy-7-methoxy-3-oxo-3,4-dihydro-2H-1,4-benzoxazin-2-yl glucoside β-D-glucosidase, β-D-glucopyranosyl abscisate β-glucosidase, β-apiosyl-β-glucosidase, and hesperidin 6-O-α-L-rhamnosyl-β-D-glucosidase; glucuronidases, including β-glucuronidase, α-glucuronidase, hyaluronoglucuronidase, glucuronosyl-disulfoglucosamine glucuronidase, glycyrrhizinate β-glucuronidase, xylan α-1,2-glucuronosidase, and baicalin-β-D-glucuronidase; glycosylases including DNA-3-methyladenine glycosylase I, thymine-DNA glycosylase, DNA-deoxyinosine glycosylase, DNA-3-methyladenine glycosylase II, rRNA N-glycosylase, DNA-formamidopyrimidine glycosylase, uracil-DNA glycosylase, and double-stranded uracil-DNA glycosylase; heparanase; hexosaminidases, including β-N-hexosaminidase; idanases, including fucoidanase; idurunodases, including L-iduronidase; inulases; lactases; levanase; licheninase; dictyostelium lysozyme A; maltosidases, including glucan 1,6-α-isomaltosidase; maltotriosidases including dextran 1,6-α-isomaltotriosidase, and glucan 1,4-α-maltotriohydrolase; maltotetraohydrolases, including glucan 1,4-α-maltotetraohydrolase; maltohexaosidases, incuding glucan 1,4-α-maltohexaosidase; maltohydrolases including glucan 1,4-α-maltohydrolase;mannosidases including mannan 1,4-mannobiosidase, mannan endo-1,6-α-mannosidase, mannosyl-oligosaccharide 1,2-α-mannosidase, and glycoprotein endo-α-1,2-mannosidase; mannosidases, including α-mannosidase, β-mannosidase, mannan 1,2-(1,3)-α-mannosidase, mannan endo-1,4-β-mannosidase, mannosyl-oligosaccharide 1,3-1,6-α-mannosidase, mannan exo-1,2-1,6-α-mannosidase, mannosylglycoprotein endo-β-mannosidase, and 1,6-α-D-mannosidase; muramidases, including peptidoglycan β-N-acetylmuramidase; nucleosidases, including N-methyl nucleosidase, purine nucleosidase, inosine nucleosidase, uridine nucleosidase, AMP nucleosidase, NAD(+) nucleosidase, NAD(P)(+) nucleosidase, adenosine nucleosidase, ribosylpyrirnidine nucleosidase, deoxyribodipyrimidine endonucleosidase, NMN nucleosidase, adenosylhomocysteine nucleosidase, pyrimidine-5'-nucleotide nucleosidase, inosinate nucleosidase, 1-methyladenosine nucleosidase, and methylthioadenosine nucleosidase; octulosonidases including 3-deoxy-2-octulosonidase, and 3-deoxyoctulosonase; 3-primeverosidase; β-porphyranase; pullulanases, including isopullulanase and neopullulanase; quercitrinase; rhamnosidases, including α-L-rhamnosidase, and β-L-rhamnosidase; sialadases, including exo-α-sialadase, and endo-α-sialidase; difructose-anhydrase synthase; trehalases, including α-α-trehalase, and α-α-phosphotrehalase; xylanases, including endo-1,4-β-xylanase, endo-1,3-β-xylanase, xylan-1,4,-xylosidase, Xylan 1,3-β-xylosidase, glucuronoarabinoxylan endo-1,4-β-xylanase, and oligosaccharide reducing-end xylanase; and still further include hydrolases selected from mannosylglycerate hydrolase 4-α-D-((1→4)-α-D-glucano)trehalose trehalohydrolase, rhamnogalacturonan hydrolase, futalosine hydrolase, poly(ADP-ribose) glycohydrolase, polymannuronate hydrolase, oligoxyloglu can reducing-end-specific cellobiohydrolase, unsaturated rhamnogalacturonyl hydrolase rhamnogalacturonan galacturonohydrolase, levanbiohydrolases, 2,6-β-fructan 6-levanbiohydrolase, α-neoagaro-oligosaccharide hydrolase, protein ADP-ribosylarginine hydrolase, ADP-ribosyl-dinitrogen reductase hydrolase, rhamnogalacturonan rhamnohydrolase, α-D-xyloside xylohydrolase, gellan tetrasaccharide unsaturated glucuronyl hydrolase, and unsaturated chondroitin disaccharide hydrolase.

Further hydrolases that may be used in accordance herewith include carboxylesterase; arylesterase; triacylglycerol lipase; phospholipase $A_2$; lysophospholipase; acetylesterase; acetylcholinesterase; actylcholine acetylhydrolase; cholinesterase; tropinesterase; pectinesterase; sterol esterase; chlorophyllase; thioester hydrolase including acetyl-CoA hydrolase; succinyl-CoA hydrolase; glutathione thiolesterase; choloyl-CoA hydrolase; phosphoric-monoester hydrolase; alkaline phosphatase; acid phosphatase; phosphoserine phosphatase; phosphatidate phosphatase; 5'-nucleotidase, 3'-nucleotidase; phytase; phosphatases including glucose phosphatase, tre-halose phosphatase, histidinol-phosphatase, phosphoprotein phosphatase, sugar-phosphatase, inositol-phosphate phosphatase, 4-nitrophenylphosphatase, protein-tyrosine-phosphatase, sorbitol-6-phosphatase; and pyridoxal phosphatase; phosphodiesterase I; phospholipase D; 3'5'-cyclic-nucleotide ph osphodiesterase; dGTPase; sulfatases, including arylsulfatase, steryl-sulfatase, glycosulfatase, choline-sulfatase, and iduronate-2-sulfatase; prenyl-diphosphatase; sclareol cyclase; ether hydrolase; adenosylhomocysteinase; cholesterol-5,6-oxide hydrolase; peptidases, including aminopeptidase, cystinyl peptidase, tripeptide aminopeptidase, prolyl aminopeptidase, glutamyl peptidase, bacterial leucyl aminopeptidase, clostridial aminopeptidase, cytosol alanyl aminopeptidase, tryptophanyl aminopeptidase, methionyl aminopeptidase, aspartyl aminopeptidase, dipeptidases, serine-type carboxypeptidases, and metallocarboxypeptidases; cathepsin; ubiquitinyl hydrolase; chymotrypsin; trypsin; thrombin; glutaminase; asparaginase; amidase; urease; arylformamidase; biotinidase; aminoacylase; nicotinamidase; glutaminase; pentanamidase; barbiturase; lactamase; creatininase; enamidase; arginase; deaminases, including adenine deaminase, adenosine deaminase, ADP deaminase, ATP deaminase, CMP deaminase, CTP and deaminase guanosine deaminase; nitrilase; arylacetonitrilase; thiocyanate hydrolase; riboflavinase; inorganic diphosphatase; apyrase; nucleotide diphosphatase; FAD diphosphatase; ADP-sugar diphosphatase; thiamine-triphosphatase; UDP-sugar diphosphatase; adenylylsulfatase; alkylhalidase; haloacetate dehalogenase; atrazine chlorohydrolase; phosphoamidase; cyclamate sulfohydrolase; ph osphonoacetate hydrolase; and trithionate hydrolase.

Still further hydrolases that may be used in accordance herewith are any hydrolases within the class of enzymes belonging to Enzyme Commission numbers 1 and 3, (EC1; EC3), and preferably those belonging to EC3. In more preferred embodiments enzymes belonging to EC 3.1 are used, including those belonging to EC 3.1.1, EC 3.1.2, EC 3.1.3, EC 3.1.4, EC 3.1.5, EC 3.1.6, and EC 3.1.7; EC 3.2; EC 3.3, including EC 3.3.1, EC 3.4, EC 3.4.11, EC 3.4.13, EC 3.4.16, EC 3.4.17, EC 3.4.18; EC 3.5, including EC 3.5.2, EC 3.5.3, EC 3.5.4, EC 3.5.5, 3.5.99; EC 3.6, including EC 3.6.1, EC 3.6.2; EC 3.8, including EC 3.8.1; EC 3.9, including EC 3.9.1; EC 3.10, including EC 3.10.1; EC 3.11, including EC 3.11.1; and EC 3.12, including EC 3.12.1.

In preferred embodiments hydrolases are selected from the class of enzymes belonging to EC 3.2.1 and 3.2.2, and more preferably, EC 3.2.1.1, EC 3.2.1.2, EC 3.2.1.3, EC 3.2.1.4, EC 3.2.1.6, EC 3.2.1.7, EC 3.2.1.8, EC 3.2.1.10, EC 3.2.1.11, EC 3.2.1.14, EC 3.2.1.15, EC 3.2.1.18, EC 3.2.1.20, EC 3.2.1.21, EC 3.2.1.22, EC 3.2.1.23, EC 3.2.1.24, EC 3.2.1.25, EC 3.2.1.26, EC 3.2.1.28, EC 3.2.1.31, EC 3.2.1.32, EC 3.2.1.33, EC 3.2.1.35, EC 3.2.1.36, EC 3.2.1.37, EC 3.2.1.38, EC 3.2.1.39, EC 3.2.1.40, EC 3.2.1.41, EC 3.2.1.42, EC 3.2.1.2, EC 3.2.1.43, EC 3.2.1.44, EC 3.2.1.45, EC 3.2.1.46, EC 3.2.1.47, EC 3.2.1.48, EC 3.2.1.49, EC 3.2.1.50, EC 3.2.1.51, EC 3.2.1.52, EC 3.2.1.53, EC 3.2.1.54, EC 3.2.1.55, EC 3.2.1.56, EC 3.2.1.57, EC 3.2.1.58, EC 3.2.1.59, EC 3.2.1.60, EC 3.2.1.61, EC 3.2.1.62, EC 3.2.1.63, EC 3.2.1.64, EC 3.2.1.65, EC 3.2.1.66, EC 3.2.1.67, EC 3.2.1.68, EC 3.2.1.70, EC 3.2.1.71, EC 3.2.1.72, EC 3.2.1.73, EC 3.2.1.74, EC 3.2.1.75, EC 3.2.1.76, EC 3.2.1.77, EC 3.2.1.78, EC 3.2.1.80, EC 3.2.1.81, EC 3.2.1.82, EC 3.2.1.83, EC 3.2.1.84, EC 3.2.1.85, EC 3.2.1.86, EC 3.2.1.87, EC 3.2.1.88, EC 3.2.1.89, EC 3.2.1.90, EC 3.2.1.91, EC 3.2.1.92, EC 3.2.1.93, EC 3.2.194, EC 3.2.1.95, EC 3.2.1.96, EC 3.2.1.97, EC 3.2.1.98, EC 3.2.1.99, EC 3.2.1.100, EC 3.2.1.101, EC 3.2.1.102, EC 3.2.1.103, EC 3.2.1.104, EC 3.2.1.105, EC 3.2.1.106, EC 3.2.1.107, EC 3.2.1.108, EC 3.2.1.109, EC 3.2.1.110, EC 3.2.1.111, EC 3.2.1.112, EC 3.2.1.113, EC 3.2.1.114, EC 3.2.1.115, EC 3.2.1.116, EC 3.2.1.117, EC 3.2.1.118, EC 3.2.1.119, EC 3.2.1.120, EC 3.2.1.121, EC 3.2.1.122, EC 3.2.1.123, EC 3.2.1.124, EC 3.2.1.125, EC 3.2.1.126, EC 3.2.1.127, EC 3.2.1.128, EC 3.2.1.129, EC 3.2.1.130, EC 3.2.1.131, EC 3.2.1.132, EC 3.2.1.133, EC 3.2.1.134, EC 3.2.1.135, EC 3.2.1.136, EC 3.2.1.137, EC 3.2.1.138, EC 3.2.1.139, EC 3.2.1.140, EC 3.2.1.141, EC 3.2.1.142, EC 3.2.1.143, EC 3.2.1.144, EC 3.2.1145, EC 3.2.1.146, EC 3.2.1.147, EC 3.2.1.149, EC 3.2.1.150, EC 3.2.1.151, EC 3.2.1.152, EC 3.2.1.153, EC 3.2.1.154, EC 3.2.1.155, EC 3.2.1.156, EC 3.2.1.157, EC 3.2.1.158, EC 3.2.1.159, EC 3.2.1.161, EC 3.21162, EC 3.2.1.163, EC 3.2.1.164, EC 3.2.1.165, EC 3.2.1.166, EC 3.2.1.167, EC 3.21168, EC 3.2.1.169, EC 3.2.1.170, EC 3.2.1.171, EC 3.2.1.172, EC 3.2.1.173, EC 3.21174, EC 3.2.1.175, EC 3.2.1.176, EC 3.2.1.177, EC 3.2.1.178, EC 3.2.1.179, EC 3.21180, EC 3.2.1.181, EC 3.2.1.182, EC 3.2.1.183, EC 3.2.1.184, EC 3.2.1.185, EC 3.2.1.n1, EC 3.2.1.n2, EC 3.2.1.n2, EC 3.2.1.2; and EC 3.2.2.1, EC 3.2.2.2, EC 3.2.2.3, EC 3.2.2.4, EC 3.2.2.5, EC 3.2.2.6, EC 3.2.2.7, EC 3.2.2.8, EC 3.2.2.9, EC 3.2.2.10, EC 3.2.2.11, EC 3.2.2.12, EC 3.2.2.13, EC 3.2.2.14, EC 3.2.2.15, EC 3.2.2.16, EC 3.2.2.17, EC 3.2.2.18, EC 3.2.2.19, EC 3.2.2.20, EC 3.2.2.21, EC 3.2.2.22, EC 3.2.2.23, EC 3.2.2.24, EC 3.2.2.25, EC 3.2.2.26, EC 3.2.2.27, EC 3.2.2.28, and EC 3.2.2.29.

In accordance herewith, cells comprising a chimeric construct comprising a promoter and a nucleic acid sequence encoding a reporter polypeptide comprising a hydrolase are prepared. Such cells may be any cells including, without limitation, any plant cells, animal cells, including human cells, or cells obtainable from or obtained from a microorganism, such as a bacterial cell or a fungal cell, e.g. *Saccharomyces cerevisiae*. Bacterial cells that may be used include *Escherichia coli* cells, *Bacillus* cells, *Pseudomonas* cells, *Clostridium* cells, *Xanthamonas* cells and *Staphylococcus* cells. Nucleic acid sequences may be introduced in the cell through a host cell vector suitable for expression in a host cell. The term "suitable for expression in a host cell" means that the host vector comprises genetic elements required to achieve expression of one or more polypeptides, including the reporter polypeptide comprising a hydrolase, encoded by the nucleic acid sequences introduced therein. Genetic elements that may be included in the host cell vector in this regard include a promoter, a transcriptional termination region, one or more nucleic acid sequences encoding marker genes, one or more origins of replication and the like. Generally, promoters obtained from bacterial cells are used when a bacterial host is selected in accordance herewith, while a fungal promoter is used when a fungal host is selected, a plant promoter will be used when a plant cell is selected, and so on.

In accordance herewith, a first and second promoter are selected, wherein the first and second promoter are inducible by the first and second parameter in the liquid medium. A wide variety of existing or novel promoters may be used in this regard. In preferred embodiments, the promoter is selected to be inducible by an environmental stimulus, including, without limitation: pH, the presence/absence of an organic compound, presence/absence of a toxic compound, pressure, light, sound, and the like. In a preferred embodiment, a nucleic acid sequence comprising the lacZ promoter is used, and more preferably the nucleic acid sequence comprising SEQ ID. NO:7 is used. The lacZ promoter is induced by isopropyl-β-D-thiogalactopyranoside (IPTG) present in the liquid medium. Other promoters that may be used in accordance herewith include, any synthetically produced or naturally occurring promoter including: lac promoter (also known as $P_{lac}$), $P_{rha}$ promoter (rhamnose inducible, glucose repressible), tet promoter ($P_{tet}$; tetracycline inducible), lambda cl promoter, $P_{las}$ promoter, lux promoter ($P_{lux}$), lex promoter ($P_{lex}$), $P_{Bad/araC}$ promoter, omp promoter ($P_{omp}$), cinL/cinR promoter, $P_{haA}$ (pH sensitive promoter) and a UV sensitive promoter; Further promoters include compound inducible promoters such as a copper sensitive promoter, including the cusR promoter ($P_{cusR}$), and an iron sensitive promoter, including the fecA promoter ($P_{fecA}$); further promoters that may be used include constitutive promoters a T7 promoter, σ24 promoter, σ28 promoter, σ32 promoter, σ38 promoter, and σ70 promoter (any sigma collection of promoter). Specific nucleic acid sequences of promoters that may be used in accordance herewith include SEQ.ID NO:8, SEQ.ID NO:9, SEQ.ID NO:10, SEQ.ID NO:11, SEQ.ID NO:12, SEQ.ID NO:13, SEQ.ID NO:14, SEQ.ID NO:15, SEQ.ID NO:16, SEQ.ID NO:17, SEQ.ID NO:18 SEQ.ID NO:19 SEQ.ID. NO: 20 and SEQ.ID NO: 21.

Additional novel inducible promoters may be identified, for example by screening a genetic library for such promoters. Thus, by way of example, in order to identify novel promoters that respond to a chemical compound (e.g. a toxic chemical compound) a library (e.g. a transposon library or a phage library) may be created in an organism (e.g. bacterial cells) known to metabolize the chemical compound. The transposon may be constructed to be a mobile genetic element containing a reporter gene (e.g. lacZ), a selectable marker (e.g. antibiotic resistance marker such as a tetracycline or ampicillin resistance marker), and the transposase enzyme responsible for gene insertion. By inserting the transposon randomly into the organism's genome a genetic library can be tested for inducible promoters. Isolated colonies, selected via the selectable marker cassette in the transposon, may be grown in the presence of the reporter gene and the chemical compound. Colonies in which the reporter gene is expressed comprise a promoter capable of induction by the chemical compound, which may be used to isolate the inducible promoter, or colonies may be used directly.

In further embodiments, the expression vector further may comprise genetic elements required for the integration of the vector or a portion thereof in the host cell's genome, for example if a plant host cell is used the T-DNA left and right border sequences which facilitate the integration into the plant's nuclear genome. Pursuant to the present disclosure the expression vector may further contain a marker gene. Marker genes that may be used in accordance with the present disclosure include all genes that allow the distinction of transformed cells from non-transformed cells, including all selectable and screenable marker genes. A marker gene may be a resistance marker such as an antibiotic resistance marker against, for example, kanamycin or ampicillin, or an auxotrophic marker. Screenable markers that may be employed to identify transformants through visual inspection include β-glucuronidase (GUS) and green fluorescent protein (GFP). One cell that particularly conveniently may be used is *Escherichia coli*. The preparation of the *E. coli* vectors may be accomplished using commonly known techniques such as restriction digestion, ligation, gel electrophoresis, DNA sequencing, the Polymerase Chain Reaction (PCR) and other methodologies well known to those of skill in the art. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Typically, these cloning vectors contain a marker allowing selection of transformed cells. Nucleic acid sequences may be introduced in these vectors, and the vectors may be introduced in *E. coli* by preparing competent cells, electroporation, transfection or using other well known methodologies to a person of skill in the art. *E. coli* may be grown in an appropriate medium, such as Luria-Broth medium and harvested. Recombinant expression vectors may readily be recovered from cells upon harvesting and lysing of the cells.

Further, general guidance with respect to the preparation of recombinant vectors and growth of recombinant cells, including, without limitation, *E. coli*, may be found in, for example: Sambrook et al., Molecular Cloning, a Laboratory Manual, Cold Spring Harbor Laboratory Press, 2012, Fourth Ed.

In another aspect, the present disclosure provides a cell comprising a chimeric nucleic acid sequence comprising in the 5' to 3' direction of translation as operably linked components a first nucleic acid construct comprising:
  (a) a first promoter operable in the cell; and
  (b) a nucleic acid sequence encoding a first reporter polypeptide comprising a first hydrolase capable of hydrolyzing a first substrate comprising a first electroactive analyte and a first carrier and releasing the first electroactive analyte from the carrier; and
a second nucleic acid construct comprising:
  (c) a second promoter operable in the cell; and
  (d) a nucleic acid sequence encoding a second reporter polypeptide comprising a second hydrolase capable of hydrolyzing a second substrate comprising a second electroactive analyte and a second carrier and releasing the second electroactive analyte from the carrier.

The first and second promoter may be a constitutive promoter or an inducible promoter. In a preferred embodiment, the first promoter is an inducible promoter. In a further preferred embodiment the first and the second promoter are inducible promoters. The cell may be an isolated or more or less pure cell or a cell cultured or suspended in a medium, solution, or growth medium.

In yet a further aspect, the present disclosure provides a mixture comprising two cells, the first cell comprising a first chimeric nucleic acid sequence comprising in the 5' to 3' direction of translation as operably linked components a first nucleic acid construct comprising:
  (a) a first promoter operable in the first cell; and
  (b) a nucleic acid sequence encoding a first reporter polypeptide comprising a first hydrolase capable of hydrolyzing a first substrate comprising a first carrier and a first electroactive analyte and releasing the first electroactive analyte from the carrier; and
the second cell comprising a second chimeric nucleic acid sequence comprising in the 5' to 3' direction of translation as operably linked components a first nucleic acid construct comprising:
  (c) a second promoter operable in the second cell; and
  (d) a nucleic acid sequence encoding a second reporter polypeptide comprising a second hydrolase capable of hydrolyzing a second substrate comprising a second carrier and a second electroactive analyte and releasing the second electroactive analyte from the carrier.

The first and second cells may be similar or even identical, but for the presence of the chimeric nucleic acid sequences therein, thus the first and second cells may each be *E. coli* cells, from the same or different strains. The cells also may be a mixture of two cell cultures comprising two different biological species. It will be clear to those of skill in the art that the mixture may comprise a plurality of cells genetically identical to the first and second cell.

Growth of the cells leads to production of the first and second hydrolase. In one embodiment, the hydrolase polypeptides may be recovered, isolated and separated from other components of the cell by a variety of different protein purification techniques including, e.g. ion-exchange chromatography, size exclusion chromatography, affinity chromatography, hydrophobic interaction chromatography, reverse phase chromatography, gel filtration, etc. Further general guidance with respect to protein purification may for example be found in: Cutler, P. Protein Purification Protocols, Humana Press, 2004, Second Ed. Thus a substantially pure protein may be obtained. By "substantially pure" it is meant that the protein is separated from other host cell components. In accordance here with the protein is at least 95% pure, and more preferably at least 96%, 97%, 98% or 99% pure. Such substantially pure hydrolase protein may be used to detect the presence of two or more electroactive analytes. Accordingly, the present disclosure in a further aspect includes an embodiment of a method of detecting a first and second electroactive analyte in a liquid medium, the method comprising:
  (i) contacting in a vessel the liquid medium and (a) a first substrate comprising a first electroactive analyte chemically linked to a first carrier; (b) a second substrate comprising a second electroactive analyte chemically linked to a second carrier; (c) a first reporter polypeptide comprising a first hydrolase; and (d) second reporter polypeptide comprising a second hydrolase, to form an assay mixture, wherein the first hydrolase is capable of hydrolyzing the first substrate and releasing the first electroactive analyte from the carrier and the second hydrolase is capable of hydrolyzing the second substrate and releasing the second electroactive analyte from the carrier; and
  (ii) detecting the electrical signal facilitated by the first and second electroactive analyte in the assay mixture, wherein detecting the electrical signal facilitated by the first and second electroactive analyte detects the first and second parameters in the sample.

In order to detect the first and second parameter in the sample, the electrical signal facilitated by the first and second electroactive analyte is detected and related to the presence of the first and second parameter. By the term "facilitated" it is meant that an electroactive analyte constitutes a conduit element of an electrical circuit. Thus the flow or conduct of an electrical current in a sample, to which a voltage is applied, is attained via an electroactive analyte, released from a carrier, resulting in the reduction or oxidation of the electroactive analyte.

The electrical signal may be detected in accordance herewith using any methodology involving the application of a voltage to the assay medium. The voltage may be applied potentiostatically (i.e. at one voltage) or in cyclic voltammetrical fashion (i.e. across a range of defined voltages). This further includes any voltamperometric methodology, including, without limitation, pulse voltammetry, linear sweep voltammetry, chromoamerometry, staircase voltammetry, and cyclical voltammetry, and variations or adaptations thereof such as differential pulse voltammetry, or wave based voltammetry with chronoamperometric steps included in the sweeps. In accordance herewith, the application of voltage to the assay medium results in the oxidation or reduction of the electroactive analyte and gain or release of electrons by the electroactive analyte or the electrode, which can be measured amperometrically in the form of a current. Voltages may be applied to a solution versus any stable reference electrode, including, without limitation, Ag/AgCl, saturated calomel electrode (SCE), saturated sodium chloride calomel electrode (SSCE), and the reduction of hydrogen electrode (RHE), and the voltage is between the production of oxygen from water at the positive end of the spectrum, and the production of hydrogen from water at the negative end. Voltages may be applied, for example, in the range from 0-2.0 V versus a reduction hydrogen electrode (RHE electrode) reference electrode, or −1 Volt to +1 Volt against a pseudo Ag/AgCl electrode. Amperages detected may range, for example, from 1 nA to 1 μA or more when a potentiostatic voltage is applied, or from about 1 nA to 10 μA or more when using cyclic voltammetry. Detection of the electrical signal in accordance with the herein disclosed methodologies involves the use of a single electrochemical cell, which is introduced in a single vessel, e.g. a single flask, tube, beaker, well plate or any other receptacle of any geometry or shape, comprising the assay mixture. The electrical cell generally comprises one or more working electrodes, a reference electrode, and a counter electrode. Further generally included is a potentiostat to control the electric cell. The composition of each of the electrodes in the electrochemical cell may vary, and depending on the composition of the reference electrode, the voltage measurements may change. The reference electrode may be any electrode that holds a consistent voltage when placed into the electrochemical cell, and is suitably a Ag/AgCl, saturated calomel electrode (SCE), or a saturated sodium chloride calomel electrode (SSCE). The counter electrode may, for example, be a gold or platinum electrode, or a carbon electrode, e.g. a printed carbon, glassy carbon or Vulcan carbon electrode. The composition of the working electrode may vary in composition, and, for example, be gold, platinum or carbon. Examples of preferred combinations of electrodes include: gold working electrode, reduction of hydrogen reference electrode, and a platinum counter electrode; glassy carbon working electrode, carbon counter electrode, and Ag/Aga reference electrode; and platinum working electrode, gold counter electrode, SCE reference electrode. It is further advantageous that the electrode is coated e.g. by thiolate self-assembled monolayers on a metal surface (e.g. gold), and/or protected, for example, a carbon electrode may be protected by applying phthalocyanine layer, by application of certain ions or metals, e.g. nickel, which may be dried on the electrode surface or platinum which may be plated on the surface. Combinations of the foregoing may also be applied.

The electrochemical cell may be calibrated prior to initiating detection. This may conveniently be done using solutions comprising the first and second electroactive analyte. Voltage can be applied through various techniques, such as cyclic voltammetry, pulse voltammetry, square wave voltammetry, potentiostatically or any other form of voltamperometric methodologies and techniques. Amperages may be detected and obtained as desired, for example in the form of a voltammogram, or chronoamperometrically. Thus, it will be clear to those of skill in the art, that in accordance with the present disclosure, the first and second parameter in the assay medium are detected by relating the electrical signal to the presence of the first and second parameter in the assay mixture. As hereinbefore mentioned, voltages are preferably selected in accordance with the distinct redox properties of the electroactive analytes. In certain embodiments, an electrical signal is only detected once per assay mixture. In other embodiments hereof, a plurality of electrical signals is detected either at regular or irregular time intervals, or detection of the electrical signals may be conducted more or less continuously. For example, where the method of the present disclosure is used to detect a first and second nutritional compound in a growth medium in order to determine depletion thereof, repeated or continuous detection may be desirable. In yet another embodiment, samples are drawn from a liquid medium to form the assay mixture. It is further noted that detection using the methods of the present disclosure may be automated, and the electrochemical cell may be linked to a computer system to control the electrochemical cell and to record and analyze the electrical signal.

Flow of an electrical current and detection thereof, upon application of a voltage to the assay medium, thus signals the presence of the first and second parameter in the assay sample. Conversely, the absence of an electrical signal, upon the application of a voltage to the assay medium, is indicative of the absence of the first and second parameter in the assay sample. In this manner, the detection of the electrical signal, in accordance with the present disclosure, correlates with and detects the first and second parameter.

In yet another aspect, the present disclosure also relates to a diagnostic kit and provides at least one embodiment of a diagnostic kit for simultaneously detecting two parameters comprising:
  (i) a cell comprising a chimeric nucleic acid sequence comprising in the 5' to 3' direction of translation as operably linked components a first nucleic acid construct comprising:
    (a) a first promoter operable in the cell; and
    (b) a nucleic acid sequence encoding a first reporter polypeptide comprising a first hydrolase capable of hydrolyzing a first substrate comprising a first electroactive analyte and a first carrier and releasing the first electroactive analyte from the carrier; and
  a second nucleic acid construct comprising:
    (c) a second promoter operable in the cell; and
    (d) a nucleic acid sequence encoding a second reporter polypeptide comprising a second hydrolase capable of hydrolyzing a second substrate comprising a second electroactive analyte and a second carrier and releasing the second electroactive analyte from the carrier;
  (ii) a first and second substrate; and
  (iii) instructions for use or storage of the kit.

The kit may be provided in such a manner that it comprises one or more more vessels, e.g. flasks, beakers, tubes, well plates, or microfluidic based device. The kit further may also be constructed in such a manner that it contains two cells: (I) a first cell comprising a chimeric nucleic acid sequence comprising in the 5' to 3' direction of translation as operably linked components a first nucleic acid construct comprising: a first promoter operable in the cell; and a nucleic acid sequence encoding a first reporter polypeptide comprising a first hydrolase capable of hydrolyzing a first substrate and producing a first electroactive analyte; and (II) a chimeric nucleic acid sequence comprising in the 5' to 3' direction of translation as operably linked components a second nucleic acid construct comprising a second promoter operable in the cell; and a nucleic acid sequence encoding a second reporter polypeptide comprising a second hydrolase capable of hydrolyzing a second substrate and producing a second electroactive analyte. The kit further may further be fabricated to comprise an electrochemical cell and/or a potentiostat.

Use of the Assays

The liquid medium as used herein can be any liquid medium including any aqueous solution, for example any buffer or salt solution, or any organic solution. In certain embodiments the medium may be an LB medium or more preferably an M9 minimal medium which are commonly used to grow *E. coli* bacterial cells. The first and second parameters in the liquid medium are two distinct parameters, for example, light and temperature, or ionic strength and temperature. In particularly preferred embodiments, the two parameters are two distinct chemical compounds. These compounds may be any chemical compounds and may be obtainable from any source, including from any liquid, gas or a solid, as desired. In embodiments where the compounds of interest are present in a liquid assay sample the compounds may be detected directly in the liquid sample, however where the compounds of interest are present in a gaseous sample or solid sample, the compounds are dissolved in a liquid medium prior to initiating detection thereof. As hereinbefore mentioned, the methods of the present disclosure permit the simultaneous detection of the presence of two parameters. It is noted however that the methodologies further permit the detection of a plurality of parameters, e.g. 3, 4, 5, 6, 7, 8, 9, 10 or more parameters. Thus when reference is made herein to a method involving the detection of a first and second parameter, it is intended that the methodology disclosed herein involves the detection of at least two parameters.

In further preferred embodiments, a first and second toxic compound found in the environment are detected, for example toxic compounds that may be present in e.g. in surface water or sediments, including for example compounds found in tailings ponds associated with mining or fossil fuel production, or toxic compounds associated with petroleum extraction, such as hydrocarbons and naphthenic acid, which may be released in the environment, for example, as a result of a pipeline or fracking well leak. In other embodiments, the chemical compounds are nutritional compounds used, e.g. nutritional compounds used by a microorganism culture, or toxins which accumulate in a microorganism's production system. It will be clear to those of skill in the art that the methodologies herein provided are independent of the exact parameters, including chemical compounds, to be detected. The first and second parameter, or the chemical formula of the first and second chemical compound does not matter and any chemical compound, or any parameter for which the presence of a compound serves as a proxy, may be detected in accordance with the methods provided by the instant disclosure.

EXAMPLES

Hereinafter are provided examples of specific embodiments for performing the methods of the present disclosure, as well as embodiments representing the compositions of the present disclosure. The examples are provided for illustrative purposes only, and are not intended to limit the scope of the present disclosure in any way.

Example 1—Detection of CPR Using Constitutively Expressed β-Galactosidase

Figure 2:
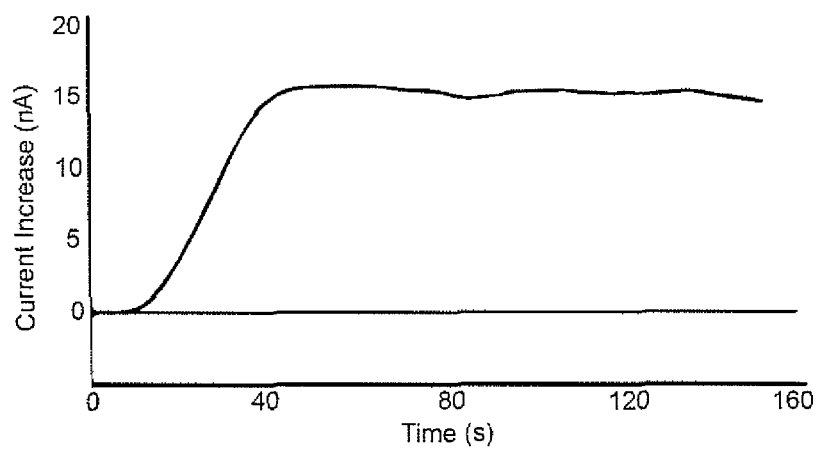
FIG. 2 depicts a graph of a chronoamperometric measurement of the enzymatic conversion of the CPRG to CPR.

For the potentiostatic detection of CPR as a product of the cleavage of CPRG by β-galactosidase, a solution of 0.1 M pH 7 sodium phosphate buffer was used. 20 mL of this solution was placed into an electrochemical cell with a screen printed carbon electrode (Pine Instruments, USA) as the working electrode, a platinum mesh as the counter electrode, and a reduction of hydrogen reference electrode (RHE) immersed in an identical solution with constant hydrogen gas bubbling and connected via a luggin capillary. The buffer was bubbled with nitrogen for 15 minutes prior to use. 1 mL of an overnight culture of *Pseudomonas fluorescens* PFS constitutively expressing lacZ via a transposon insertion was pelleted and resuspended in 0.1 M pH 7 phosphate buffer and then added to the electrochemical cell. The working electrode was then held at 1.325V vs RHE and the current allowed to stabilize for 1200 seconds. After stabilization the substrate CPRG was added to the solution (time zero in FIG. 2) and the current produced at the working electrode was recorded. FIG. 2 provides the results obtained.

Example 2—Detection of PNP Using Constitutively Expressed β-Glucuronidase

Figure 4:
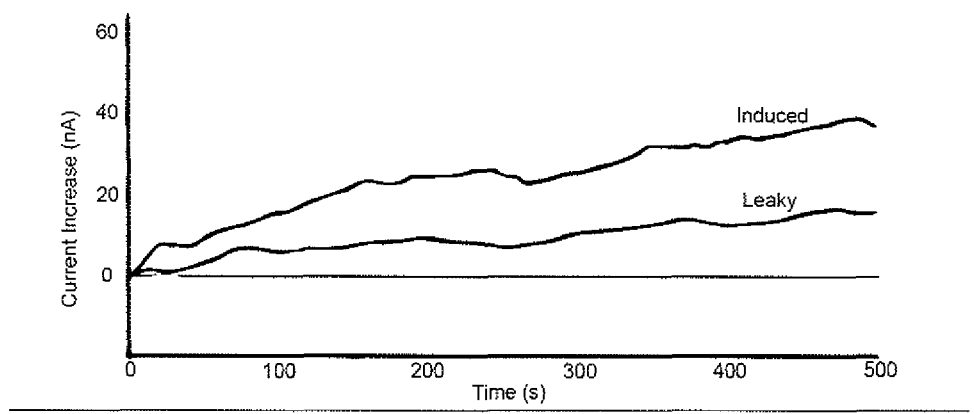
FIG. 4 depicts a graph of a chronoamperometric measurement of the enzymatic conversion of PNPG to PNP.

For the potentiostatic detection of PNP as a product of the cleavage of PNPG by β-glucuronidase, a solution of 0.1 M pH 7 sodium phosphate buffer was used. 20 mL of this solution was placed into an electrochemical cell with a screen printed carbon electrode (Pine Instruments, USA) as the working electrode, a platinum mesh as the counter electrode, and a reduction of hydrogen reference electrode (RHE) immersed in an identical solution with constant hydrogen gas bubbling and connected via a luggin capillary. The buffer was bubbled with nitrogen for 15 minutes prior to use. 1 mL of an overnight culture of TOP10 *E. coli* expressing uidA under the control of the LacI repressible promoter on a high copy number plasmid (PSB1C3) was pelleted and resuspended in 0.1 M pH 7 phosphate buffer and then added to the electrochemical cell. One sample was treated with 500 μM IPTG during the overnight culture, while the second was grown without induction to assess basal (leaky) expression in the genetic circuit. The working electrode was then held at 1.6 V vs RHE for each sample and the current allowed to stabilize for 1200 seconds. After stabilization the substrate PNPG was added to the solution (time zero in FIG. 4) and the current produced at the working electrode was recorded. FIG. 4 provides the results obtained.

Example 3—Detection of PDP Using Inducibly Expressed β-Glucosidase

Figure 3:
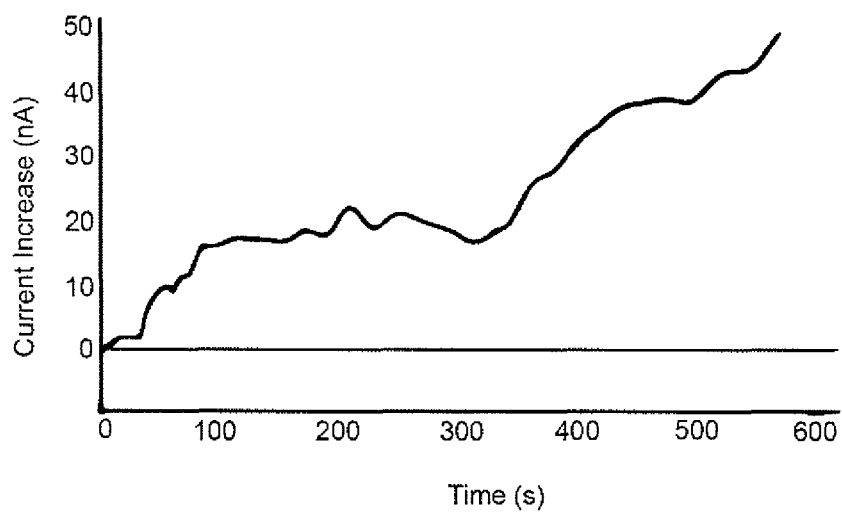
FIG. 3 depicts a graph of a chronoamperometric measurement of the enzymatic conversion of PDPG to PDP.

For the potentiostatic detection of PDP as a product of the cleavage of PDPG by β-glucosidase, a solution of 0.1 M pH 7 sodium phosphate buffer was used. 20 mL of this solution was placed into an electrochemical cell with a screen printed carbon electrode (Pine Instruments, USA) as the working electrode, a platinum mesh as the counter electrode, and a reduction of hydrogen reference electrode (RHE) immersed in an identical solution with constant hydrogen gas bubbling and connected via a luggin capillary. The buffer was bubbled with nitrogen for 15 minutes prior to use. 1 mL of an overnight culture of TOP10 *E. coli* expressing native levels of bglX when grown in rich media was pelleted and resuspended in 0.1 M pH 7 phosphate buffer and then added to the electrochemical cell. The working electrode was then held at 0.825V vs RHE and the current allowed to stabilize for 1200 seconds. After stabilization the substrate PDPG was added to the solution (time zero in FIG. 3) and the current produced at the working electrode was recorded. FIG. 3 shows the results obtained.

Example 4—Simultaneous Detection of PDP and CPR

Figure 5:
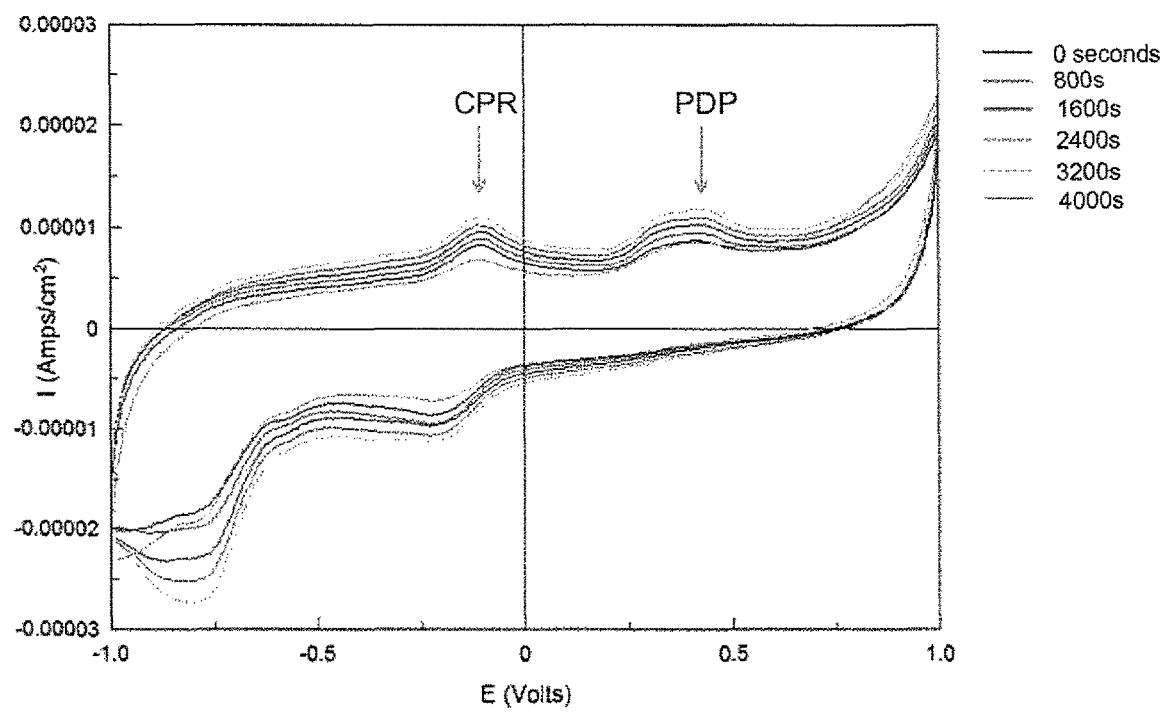
FIG. 5 depicts a voltammogram simultaneously measuring the in vivo enzymatic conversion of CPRG to CPR and PDPG to PDP.

For the simultaneous voltammetric detection of PDP and CPR at once as a product of the cleavage of PDPG and CPRG by β-glucosidase and β-galactosidase respectively, a solution of 0.1 M pH 7 sodium phosphate buffer was used. 15 mL of this solution was placed into an electrochemical cell with a screen printed carbon electrode (Pine Instruments, USA) as the working electrode, counter electrode, and a screen printed Ag/AgCl pseudo-reference electrode immersed in the same solution. The buffer was bubbled with nitrogen for 15 minutes prior to use. 2 mL of an overnight culture of BL-21 *E. coli* was pelleted and resuspended in 0.1 M pH 7 phosphate buffer and then added to the electrochemical cell. PDPG and CPRG were added to the solution and the working electrode was then swept between −1 V and 1 V vs the Ag/AgCl reference at 100 mV/s for 100 cycles. Six cycles 800 seconds apart, from the initial start of the sweep considering it to be the baseline (0 seconds), are reported in FIG. 5. Oxidation of PDP and CPR are noted (−0.2 and 0.4V respectively) as shown by the increase of peak heights after each voltammetric sweep.

Example 5—Simultaneous Detection of PDP and PNP

Figure 6:
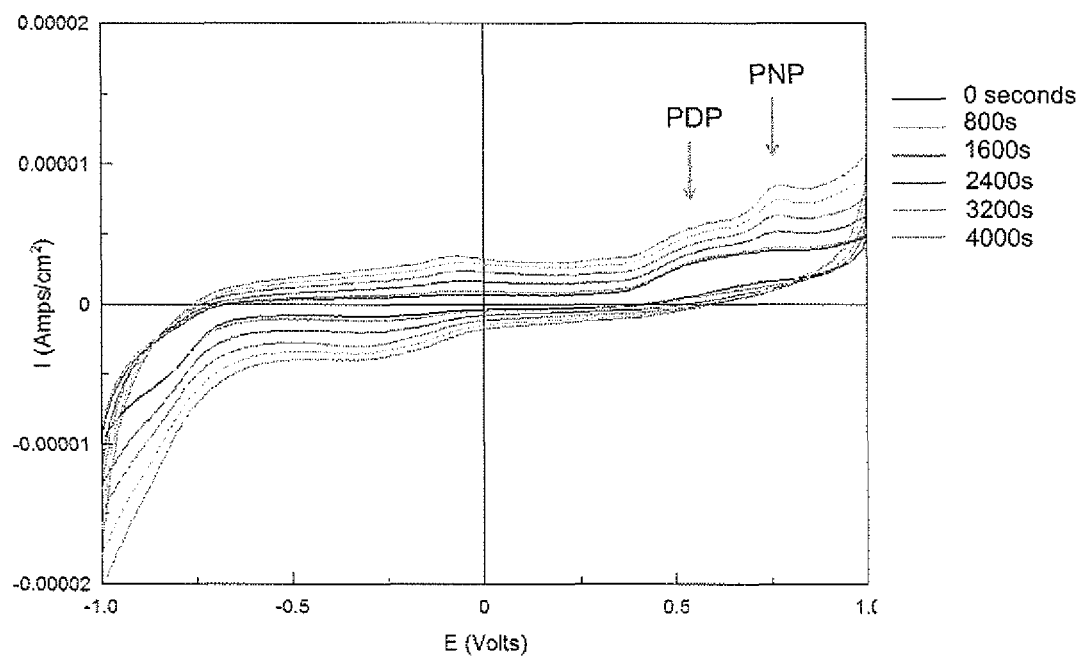
FIG. 6 depicts a voltammogram simultaneously measuring the in vivo enzymatic conversion of PDPG to PDP, and PNPG to PNP.

For the simultaneous in vivo voltammetric detection of PDP and PNP at once as a product of the cleavage of PDPG and PNPG by β-glucosidase and β-glucuronidase respectively, a solution of 0.1 M pH 7 sodium phosphate buffer was used. 15 mL of this solution was placed into an electrochemical cell with a screen printed carbon electrode (Pine Instruments, USA) as the working electrode, counter electrode, and a screen printed Ag/AgCl pseudo-reference electrode immersed in the same solution. The buffer was bubbled with nitrogen for 15 minutes prior to use. 2 mL of an overnight culture of BL-21 *E. coli* with a plasmid harbouring the uidA gene under the control of an uninduced LacI responsive promoter was pelleted and resuspended in 0.1 M pH 7 phosphate buffer and then added to the electrochemical cell. PDPG and PNPG were added to the solution and the working electrode was then swept between −1 V and 1 V vs the Ag/AgCl reference at 100 mV/s for 100 cycles. Six cycles 800 seconds apart, from the initial start of the sweep considering it to be the baseline (0 seconds), are reported in FIG. 6. Oxidation of PDP and PNP are noted (−0.2 and 0.7V respectively) as shown by the increase of peak heights after each sweep.

Example 6—Simultaneous Detection of PDP, CPR and PNP

Figure 7:
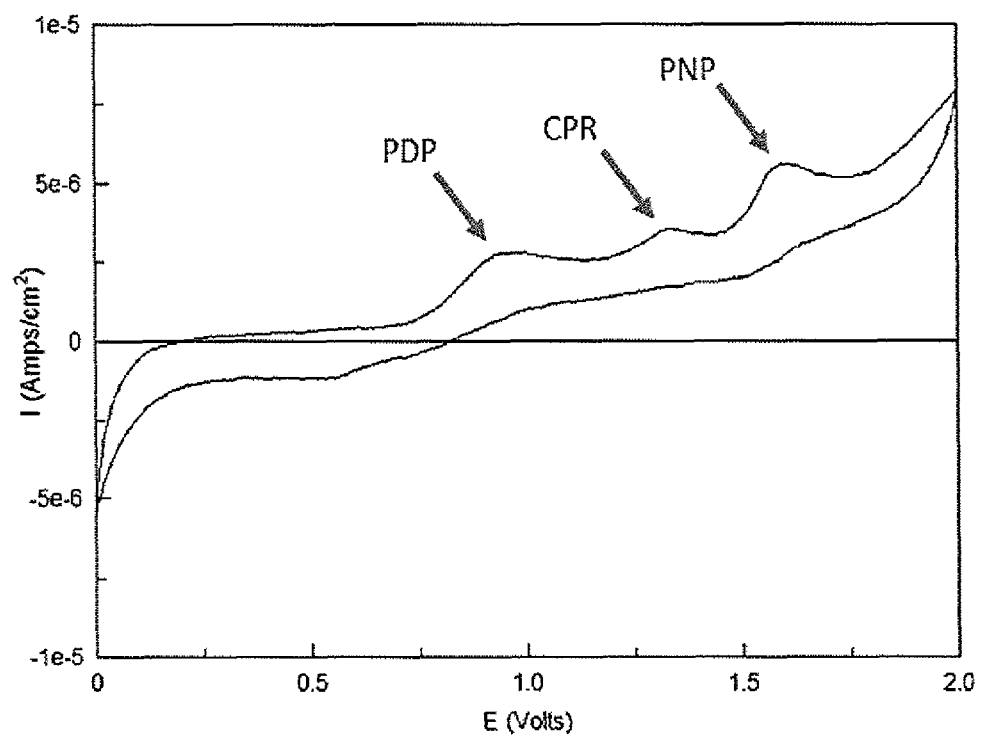
FIG. 7 depicts a voltammogram, showing simultaneous detection of PDP, PNP and CPR. Arrows indicate the presence at unique voltages of each of the electroactive analytes.

For the simultaneous in vivo voltammetric detection of PDP, CPR, and PNP at once, a solution of 0.1 M pH 7 sodium phosphate buffer was used. 15 mL of this solution was placed into an electrochemical cell with a screen printed carbon electrode (Pine Instruments, USA) as the working electrode, counter electrode, and a screen printed Ag/AgCl pseudo-reference electrode immersed in the same solution. The buffer was bubbled with nitrogen for 15 minutes prior to use. 0.2 mL of 2 mM PDP and PNP was added to the solution as well as 0.5 mL of 0.001% (w/v) CPR. After mixing the working electrode was then swept between −1 V and 1 V vs the Ag/AgCl reference at 100 mV/s for 3 cycles. Results are shown in FIG. 7.

Example 7—Detection of PDP Using Inducibly Expressed β-Glucuronidase

Figure 8:
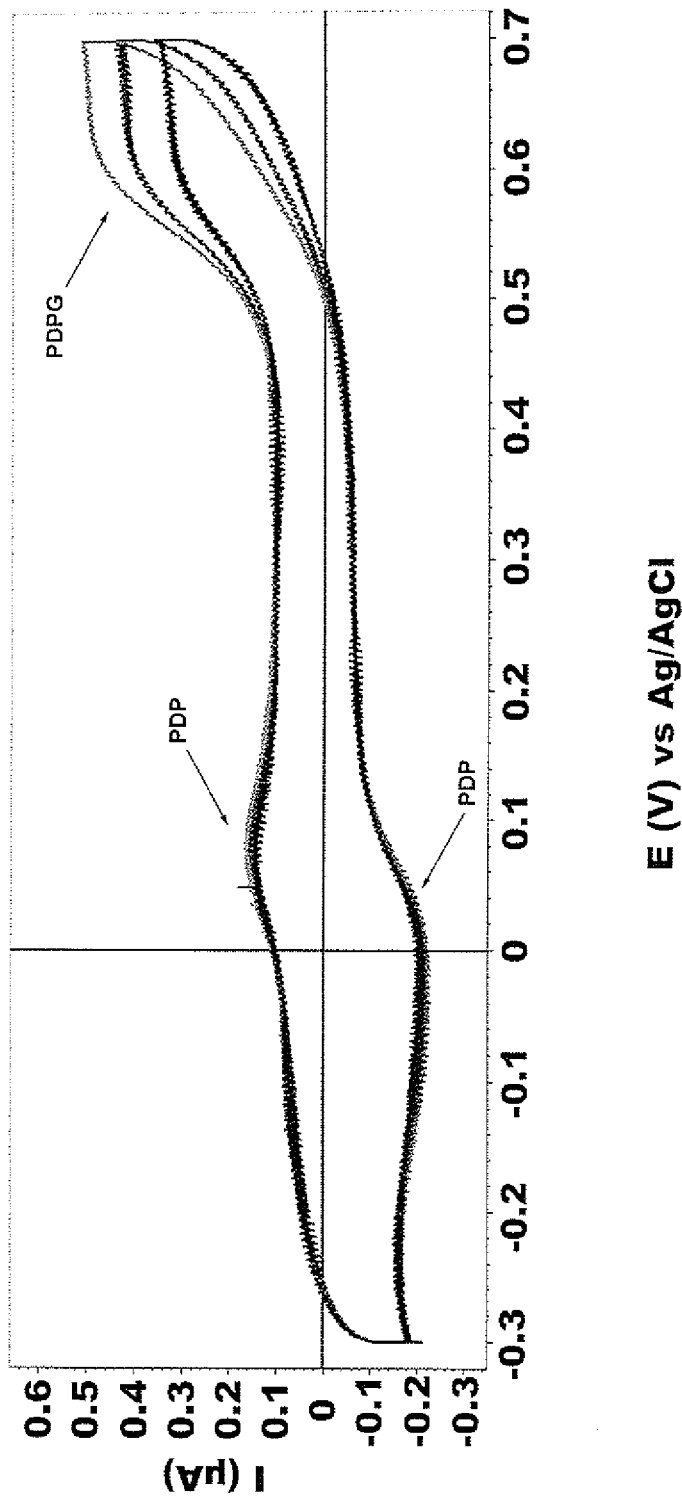
FIG. 8 depicts a voltammogram measuring the in vivo enzymatic conversion of PDPG to PDP following induction of β-glucuronidase expression in E. coli. Various sweeps are shown. The ten minute (black), twenty minute (blue), and thirty minute (red) sweeps show the growth of a PDP peak in both maximum current and charge over time.

For the observation of PDP produced from an inducible promoter translating the UidA protein from *E. coli* (JM109 K-12), a solution of 0.1 M pH 7 sodium phosphate buffer was used. 10 mL of this solution was used to immerse a glassy carbon electrode with a Pt mesh counter electrode and a Ag/AgCl reference. 2 mL of transformed cells (with rhamnose promoter $P_{Rha}$ inducible uidA protein) were grown for 4 hours at 37 degrees, induced with a genetic circuit activating component (1% w/v rhamnose) for 6 hours, and then pelleted and rinsed in the phosphate buffer pH 7.0 three times. The cells were subsequently added to a tube containing 5 mM PDPG and 50 µL was added every ten minutes to the electrochemical cell for thirty minutes. At each concentration, the working electrode was then swept from −0.3 V to 0.7 V vs the Ag/AgCl reference electrode at 100 mV/s for 3 cycles and the third cycle was plotted. A voltammogram showing the results is provided in FIG. 8.

Example 8—Detection of PAP Using Inducibly Expressed β-Galactosidase

Figure 9:
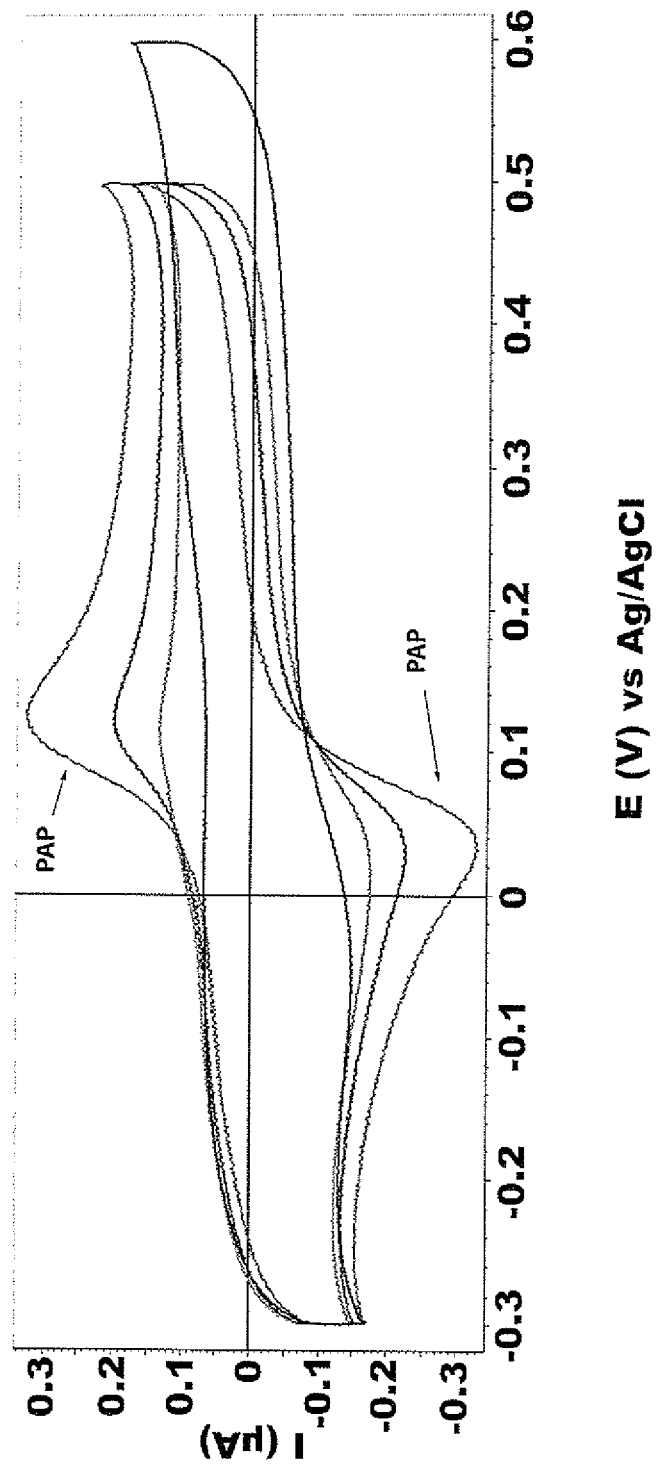
FIG. 9 depicts a voltammogram measuring the in vivo enzymatic conversion of PAPG to PAP following induction of β-galactosidase expression in E. coli. Various sweeps are shown. The baseline (black), ten minute (red), twenty minute (blue), and thirty minute (green) sweeps show the growth of a PAP peak in both maximum current and charge over time.

For the observation of PAP produced from an inducible promoter translating the LacZ protein from *E. coli* (DH5 α K-12) a solution of 0.1 M pH 7 sodium phosphate buffer was used. 10 mL of this solution was used to immerse a glassy carbon electrode with a Pt mesh counter electrode and a Ag/AgCl reference. 2 mL of transformed cells (with an IPTG inducible promoter $P_{lac}$ inducible lacZ protein) were grown for 4 hours at 37 degrees, induced with a genetic circuit activating component (1 mM final concentration IPTG) for 6 hours, and then pelleted and rinsed in the phosphate buffer pH 7.0 three times. The cells were subsequently added to a tube containing 5 mM PAPG and 50 µL was added every ten minutes to the electrochemical cell for thirty minutes. At each concentration, the working electrode was then swept from −0.3 V to 0.5 V vs the Ag/AgCl reference electrode at 100 mV/s for 3 cycles and the third cycle was plotted (the baseline was extended to 0.6 V to check for additional voltammogram features). A voltammogram showing the results is provided in FIG. 9.

Figure 10:
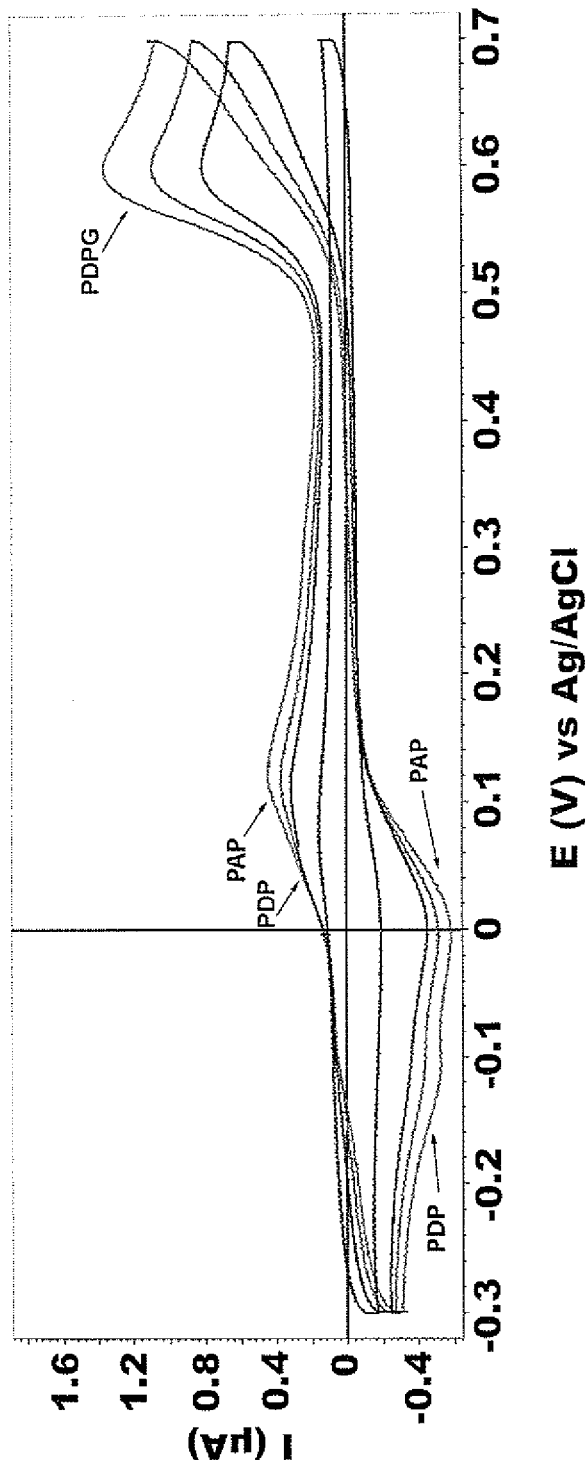
FIG. 10 depicts a voltammogram simultaneously measuring the in vivo enzymatic conversion of PAPG to PAP following induction of β-galactosidase expression and PNPG to PNP following induction of β-glucuronidase expression in E. coli. The baseline (black), ten minutes (blue), twenty minutes (green), and thirty minutes (red) sweeps show the growth of both PDP and PAP peaks in both maximum current and charge over time.

Example 9—Simultaneous Detection of PDP and PAP Using Inducibly Expressed β-Galactosidase and Inducibly Expressed β-Glucuronidase For the observation of both PDP and PAP produced from two inducible promoters translating the LacZ and UidA proteins from *E. coli* ($P_{lac}$ and $P_{Rha}$ promoters, respectively), a solution of 0.1 M pH 7 sodium phosphate buffer was used. 10 mL of this solution was used to immerse a glassy carbon electrode with a Pt mesh counter electrode and a Ag/AgCl reference. 2 mL of transformed cells were grown overnight (as previously described), induced with a genetic circuit activating component specific for each transformed gene (1 mM IPTG for the $P_{lac}$ promoter and 1% (w/v) rhamnose for the $P_{Rha}$ promoter), and then pelleted and rinsed in the phosphate buffer. The cells were subsequently added to a tube containing 5 mM PAPG and 5 mM PDPG, and 50 µL was added every ten minutes to the electrochemical cell for thirty minutes. At each concentration, the working electrode was then swept from −0.3 V to 0.7 V vs the Ag/AgCl reference electrode at 100 mV/s for 3 cycles and the third cycle was plotted. A voltammogram showing the results is provided in FIG. 10.

Figure 11:
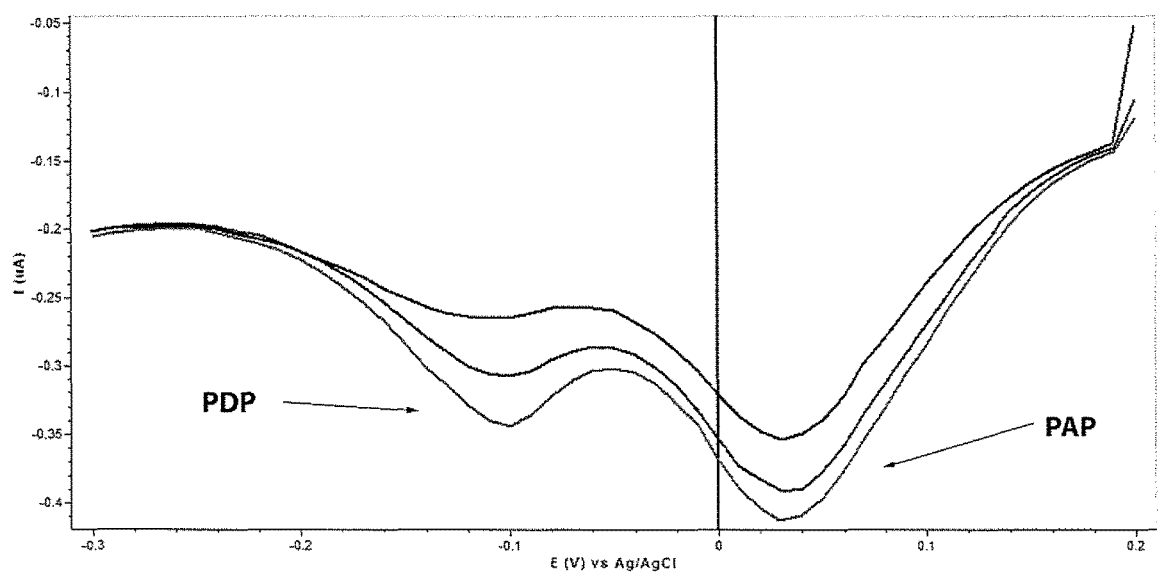
FIG. 11 depicts a differential pulse voltammogram simultaneously measuring the in vivo enzymatic conversion of PAPG to PAP following induction of β-galactosidase expression and PNPG to PNP following induction of β-glucuronidase expression in E. coli. The ten minute (black), twenty minute (blue), and thirty minute (red) minute sweeps are displayed to demonstrate the growth of both PDP and PAP reduction peaks in both maximum current and charge over time.

Example 10—Simultaneous Detection of PDP and PAP Using Inducibly Expressed β-Galactosidase and Inducibly Expressed β-Glucuronidase by Differential Pulse Voltammetry For an alternate observation of PDP and PAP produced from two inducible promoters translating the LacZ and UidA proteins from *E. coli* ($P_{lac}$ and $P_{Rha}$ promoters, respectively), a solution of 0.1 M pH 7 sodium phosphate buffer was used. 10 mL of this solution was used to immerse a glassy carbon electrode with a Pt mesh counter electrode and a Ag/AgCl reference. 2 mL of transformed cells were grown overnight, induced with a genetic circuit activating component (1 mM IPTG for the Plac promoter and 1% (w/v) rhamnose for the $P_{Rha}$ promoter) specific for each transformed gene, and then pelleted and rinsed in the phosphate buffer. The cells were subsequently added to a tube containing 5 mM PAPG and 5 mM PDPG, and 50 µL was added every ten minutes to the electrochemical cell for thirty minutes. At each concentration, the working electrode was held at 0.2 V vs Ag/AgCl for ten seconds and then pulsed negatively to −0.3 V vs Ag/AgCl using the differential pulse voltammetry method. The pulse height used was 5 mV for 50 ms, with a step width of 10 mV for 100 ms. A differential pulse voltammogram showing the results is provided in FIG. 11.

Example 11—Comparison of Induced Versus Non-Induced β-Galactosidase

Figure 12:
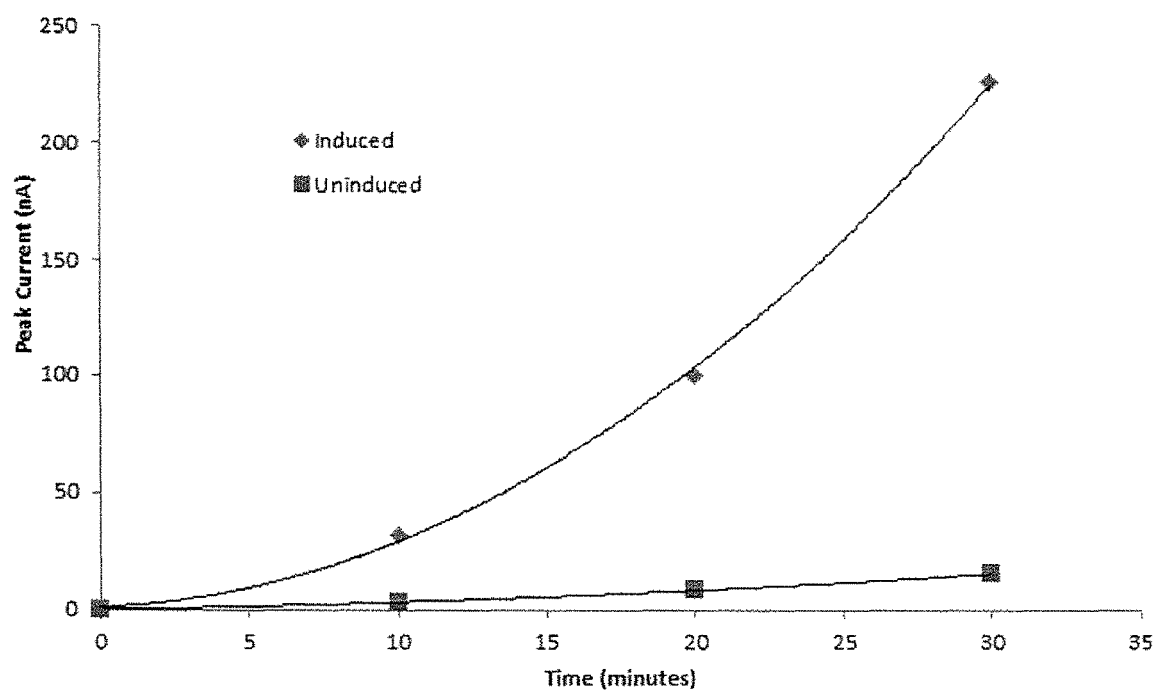
FIG. 12 depicts a graph showing the maximum current in the oxidation peak of PAP calculated and plotted as a function of time. Compared are *E. coli* cells induced to produce β-galactosidase and convert PAPG to PAP versus non-induced *E. colil* cells. Induced cells are represented by the blue diamonds and non-induced cells are represented by the red squares.

To compare the production of PAP from an inducible bacteria translating the LacZ protein from *E. coli* under the control of an inducible promoter, Mac, a solution of 0.1 M pH 7 sodium phosphate buffer was used. 10 mL of this solution was used to immerse a glassy carbon electrode with a Pt mesh counter electrode and a Ag/AgCl reference, 2 mL of transformed cells were grown overnight, induced with a genetic circuit activating component (1 mM IPTG) specific for the transformed gene or left non-induced, and then pelleted and rinsed in the phosphate buffer. The cells were subsequently added to a tube containing 5 mM PAPG, and 50 µL was added every ten minutes to the electrochemical cell for thirty minutes. At each concentration the working electrode was swept from −0.3 V to 0.7 V vs Ag/AgCl for three cycles. The maximum current in the oxidation peak of PAP was calculated for each sample and plotted as a function of time (occurring at approximately 0.1 V). The results are shown in FIG. 12.

Figure 13:
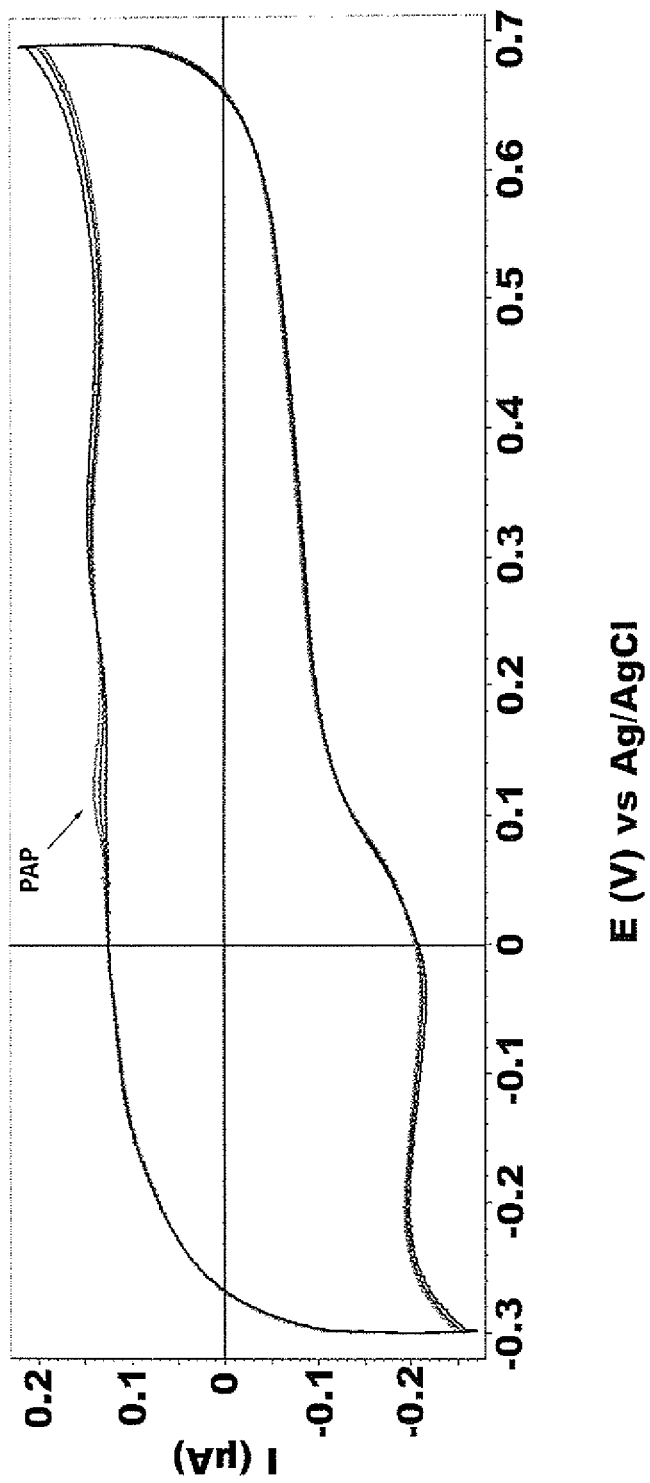
FIG. 13 depicts a voltammogram showing baseline production of PAP in *E. coli* comprising an inducible promoter under non-induced conditions. The ten (black), twenty (blue), and thirty (red) minute sweeps are displayed to demonstrate the minimal growth of a PAP peak in both maximum current and charge over time.

Example 12—Baseline Production of PAP from *E. coli* Capable of Inducibly Producing β-Galactosidase For the observation of the baseline production of PAP from an inducible promoter capable of translating the LacZ protein from *E. coli*, under non-induced conditions, a solution of 0.1 M pH 7 sodium phosphate buffer was used. 10 mL of this solution was used to immerse a glassy carbon electrode with a Pt mesh counter electrode and a Ag/AgCl reference. 2 mL of transformed cells were grown overnight and then pelleted and rinsed in the phosphate buffer. The cells were subsequently added to a tube containing 5 mM PAPG and 50 µL was added every ten minutes to the electrochemical cell for thirty minutes. At each concentration, the working electrode was then swept from −0.3 V to 0.7 V vs the Ag/AgCl reference electrode at 100 mV/s for 3 cycles and the third cycle was plotted. The results are shown in FIG. 13.

All publications, patents and patent applications are herein incorporated by reference in their entirety to the same extent as if each individual publication, patent or patent application was specifically and individually indicated to be incorporated by reference in its entirety.

We claim as our invention:

1. A diagnostic kit for simultaneously detecting two parameters comprising:
  (i) a cell comprising a chimeric nucleic acid sequence comprising in the 5' to 3' direction of translation as operably linked components a first nucleic acid construct comprising:
    (a) a first promoter operable in the cell; and
    (b) a nucleic acid sequence encoding a first reporter polypeptide comprising a first hydrolase capable of hydrolyzing a first substrate comprising a first electoactive analyte and a first carrier and releasing the first electroactive analyte from the carrier; and
  a second nucleic acid construct comprising:
    (c) a second promoter operable in the cell; and
    (d) a nucleic acid sequence encoding a second reporter polypeptide comprising a second hydrolase capable of hydrolyzing the second substrate comprising a second electroactive analytes and a second carrier and releasing the second electroactive analyte from the carrier;
  (ii) a first and second substrate; and
  (iii) instructions for use or storage of the kit, wherein the first and second hydrolase are independently selected from the group of hydrolases consisting of β-D-glucosidase, β-D galactosidase, and β-D-glucuronidase, and wherein the first and second substrate are independently selected from the group of substrates consisting of chlorophenol red-β-D-galactopyranoside (CPRG), para-nitrophenol-β-D-glucuronide (PNPG) and para-diphenol-β-D-glucopyranoside (PDPG).

2. The kit according to claim 1 wherein the first and second hydrolase are independently selected from SEQ.ID. NO:2, SEQ.ID. NO:4 and SEQ.ID. NO:6.

3. The kit according to claim 1, wherein the kit is operable in conjunction with an electrical cell.

4. The kit according to claim 3 wherein the electrical cell is capable of detecting by voltammetric sweep an electrical signal facilitated by the first and second electroactive analyte in an assay mixture containing the cell and the first and second substrate.

5. The kit according to claim 1 wherein the first and second parameters are a first and second chemical compound.

6. The kit according to claim 5 wherein the first and second chemical compounds are toxic compounds present in surface water or sediments.

7. The kit according to claim 5 wherein the first and second chemical compounds are nutritional compounds used by a microorganism culture.

8. A cell comprising a chimeric nucleic acid sequence comprising in the 5' to 3' direction of translation as operably linked components a first nucleic acid construct comprising:
(a) a first promoter operable in the cell; and
(b) a nucleic acid sequence encoding a first reporter polypeptide comprising a first hydrolase capable of hydrolyzing a first substrate comprising a first electroactive analyte and a first carrier and releasing the first electroactive analyte from the carrier; and
a second nucleic acid construct comprising:
(c) a second promoter operable in the cell; and
(d) a nucleic acid sequence encoding a second reporter polypeptide comprising a second hydrolase capable of hydrolyzing the second substrate comprising a second electroactive analyte and a second carrier and releasing the second electroactive analyte from the carrier, wherein the first and second hydrolase are independently selected from the group of hydrolases consisting of β-D-glucosidase, β-D galactosidase, and β-D-glucuronidase, and wherein the first and second substrate are independently selected from the group of substrates consisting of chlorophenol red-β-D-galactopyranoside (CPRG), para-nitrophenol-β-D-glucuronide (PNPG), para-aminophenol-β-D-galactopyranoside (PAPG) and para-diphenol-β-D-glucopyranoside (PDPG).

9. The cell according to claim 8 wherein the first and second promoter are an inducible promoter.

10. The cell according to claim 8 wherein the first and second hydrolase are independently selected from SEQ.ID. NO:2, SEQ.ID. NO:4 and SEQ.ID. NO:6.

* * * * *

SEQUENCE LISTING

<160> NUMBER OF SEQ ID NOS: 21

<210> SEQ ID NO 1
<211> LENGTH: 3075
<212> TYPE: DNA
<213> ORGANISM: Escherichia coli

<400> SEQUENCE: 1

```
atgaccatga ttacggattc actggccgtc gttttacaac gtcgtgactg ggaaaaccct      60
ggcgttaccc aacttaatcg ccttgcagca catccccctt cgccagctg gcgtaatagc     120 gaagaggccc gcaccgatcg cccttcccaa cagttgcgca gcctgaatgg cgaatggcgc     180
tttgcctggt ttccggcacc agaagcggtg ccggaaagct ggctggagtg cgatcttcct     240
gaggccgata ctgtcgtcgt cccctcaaac tggcagatgc acggttacga tgcgcccatc     300
tacaccaacg tgacctatcc cattacggtc aatccgccgt ttgttcccac ggagaatccg     360
acgggttgtt actcgctcac atttaatgtt gatgaaagct ggctacagga aggccagacg     420
cgaattattt ttgatggcgt taactcggcg tttcatctgt ggtgcaacgg cgctgggtc     480 ggttacggcc aggacagtcg tttgccgtct gaatttgacc tgagcgcatt tttacgcgcc     540
ggagaaaacc gcctcgcggt gatggtgctg cgctggagtg acggcagtta tctggaagat     600
caggatatgt ggcggatgag cggcatttc cgtgacgtct cgttgctgca taaaccgact     660
acacaaatca gcgatttcca tgttgccact cgctttaatg atgatttcag ccgcgctgta     720
ctggaggctg aagttcagat gtgcggcgag ttgcgtgact acctacgggt aacagtttct     780
ttatggcagg gtgaaacgca ggtcgccagc ggcaccgcgc ctttcggcgg tgaaattatc     840
gatgagcgtg tggttatgc cgatcgcgtc acactacgtc tgaacgtcga aaacccgaaa     900
ctgtggagcg ccgaaatccc gaatctctat cgtgcggtgg ttgaactgca caccgccgac     960
ggcacgctga ttgaagcaga agcctgcgat gtcggtttcc gcgaggtgcg gattgaaaat    1020
ggtctgctgc tgctgaacgg caagccgttg ctgattcgag gcgttaaccg tcacgagcat    1080
catcctctgc atggtcaggt catggatgag cagacgatgg tgcaggatat cctgctgatg    1140
aagcagaaca actttaacgc cgtgcgctgt tcgcattatc gaaccatcc gctgtggtac    1200 acgctgtgcg accgctacgg cctgtatgtg gtggatgaag ccaatattga acccacggc    1260 atggtgccaa tgaatcgtct gaccgatgat ccgcgctggc taccggcgat gagcgaacgc    1320
gtaacgcgaa tggtgcagcg cgatcgtaat cacccgagtg tgatcatctg gtcgctgggg    1380
```

-continued

```
aatgaatcag gccacggcgc taatcacgac gcgctgtatc gctggatcaa atctgtcgat    1440
ccttcccgcc cggtgcagta tgaaggcggc ggagccgaca ccacggccac cgatattatt    1500
tgcccgatgt acgcgcgcgt ggatgaagac cagcccttcc cggctgtgcc gaaatggtcc    1560
atcaaaaaat ggctttcgct acctggagag acgcgcccgc tgatcctttg cgaatacgcc    1620
cacgcgatgg gtaacagtct tggcggtttc gctaaatact ggcaggcgtt tcgtcagtat    1680
ccccgtttac agggcggctt cgtctgggac tgggtggatc agtcgctgat taaatatgat    1740
gaaaacggca accgtggtc ggcttacggc ggtgattttg gcgatacgcc gaacgatcgc    1800
cagttctgta tgaacggtct ggtctttgcc gaccgcacgc cgcatccagc gctgacggaa    1860
gcaaaacacc agcagcagtt tttccagttc cgtttatccg ggcaaaccat cgaagtgacc    1920
agcgaatacc tgttccgtca tagcgataac gagctcctgc actggatggt ggcgctggat    1980
ggtaagccgc tggcaagcgg tgaagtgcct ctggatgtcg ctccacaagg taaacagttg    2040
attgaactgc ctgaactacc gcagccggag agcgccgggc aactctggct cacagtacgc    2100
gtagtgcaac cgaacgcgac cgcatggtca gaagccgggc acatcagcgc tggcagcag    2160 tggcgtctgg cggaaaacct cagtgtgacg ctccccgccg cgtccacgc catcccgcat    2220 ctgaccacca gcgaaatgga tttttgcatc gagctgggta ataagcgttg caatttaac    2280 cgccagtcag gctttctttc acagatgtgg attggcgata aaaacaact gctgacgccg    2340 ctgcgcgatc agttcacccg tgcaccgctg gataacgaca ttggcgtaag tgaagcgacc    2400
cgcattgacc ctaacgcctg ggtcgaacgc tggaaggcgg cgggccatta ccaggccgaa    2460
gcagcgttgt tgcagtgcac ggcagataca cttgctgatg cggtgctgat tacgaccgct    2520
cacgcgtggc agcatcaggg gaaaacctta tttatcagcc ggaaaaccta ccggattgat    2580
ggtagtggtc aaatggcgat taccgttgat gttgaagtgg cgagcgatac accgcatccg    2640
gcgcggattg gcctgaactg ccagctggcg caggtagcag agcgggtaaa ctggctcgga    2700
ttagggccgc aagaaaacta tcccgaccgc cttactgccg cctgttttga ccgctgggat    2760
ctgccattgt cagacatgta tacccgtac gtcttcccga gcgaaaacgg tctgcgctgc    2820
gggacgcgcg aattgaatta tggcccacac cagtggcgcg gcgacttcca gttcaacatc    2880
agccgctaca gtcaacagca actgatgaa accagccatc gccatctgct gcacgcggaa    2940
gaaggcacat ggctgaatat cgacggttc catatgggga ttggtggcga cgactcctgg    3000
agcccgtcag tatcggcgga atttcagctg agcgccggtc gctaccatta ccagttggtc    3060
tggtgtcaaa aataa                                                    3075
```

<210> SEQ ID NO 2
<211> LENGTH: 1024
<212> TYPE: PRT
<213> ORGANISM: Escherichia coli

<400> SEQUENCE: 2

```
Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60
```

-continued

```
Pro Ala Pro Glu Ala Val Pro Glu Ser Trp Leu Glu Cys Asp Leu Pro
 65                  70                  75                  80

Glu Ala Asp Thr Val Val Pro Ser Asn Trp Gln Met His Gly Tyr
                 85                  90                  95

Asp Ala Pro Ile Tyr Thr Asn Val Thr Tyr Pro Ile Thr Val Asn Pro
            100                 105                 110

Pro Phe Val Pro Thr Glu Asn Pro Thr Gly Cys Tyr Ser Leu Thr Phe
            115                 120                 125

Asn Val Asp Glu Ser Trp Leu Gln Glu Gly Gln Thr Arg Ile Ile Phe
130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
            195                 200                 205

Ile Phe Arg Asp Val Ser Leu Leu His Lys Pro Thr Thr Gln Ile Ser
210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
            275                 280                 285

Arg Val Thr Leu Arg Leu Asn Val Glu Asn Pro Lys Leu Trp Ser Ala
290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
            355                 360                 365

Asp Glu Gln Thr Met Val Gln Asp Ile Leu Leu Met Lys Gln Asn Asn
370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
            420                 425                 430

Trp Leu Pro Ala Met Ser Glu Arg Val Thr Arg Met Val Gln Arg Asp
            435                 440                 445

Arg Asn His Pro Ser Val Ile Ile Trp Ser Leu Gly Asn Glu Ser Gly
450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Gly Ala Asp Thr Thr Ala
```

-continued

```
                485                 490                 495
Thr Asp Ile Ile Cys Pro Met Tyr Ala Arg Val Asp Glu Asp Gln Pro
                500                 505                 510
Phe Pro Ala Val Pro Lys Trp Ser Ile Lys Lys Trp Leu Ser Leu Pro
                515                 520                 525
Gly Glu Thr Arg Pro Leu Ile Leu Cys Glu Tyr Ala His Ala Met Gly
                530                 535                 540
Asn Ser Leu Gly Gly Phe Ala Lys Tyr Trp Gln Ala Phe Arg Gln Tyr
545                 550                 555                 560
Pro Arg Leu Gln Gly Gly Phe Val Trp Asp Trp Val Asp Gln Ser Leu
                565                 570                 575
Ile Lys Tyr Asp Glu Asn Gly Asn Pro Trp Ser Ala Tyr Gly Gly Asp
                580                 585                 590
Phe Gly Asp Thr Pro Asn Asp Arg Gln Phe Cys Met Asn Gly Leu Val
                595                 600                 605
Phe Ala Asp Arg Thr Pro His Pro Ala Leu Thr Glu Ala Lys His Gln
                610                 615                 620
Gln Gln Phe Phe Gln Phe Arg Leu Ser Gly Gln Thr Ile Glu Val Thr
625                 630                 635                 640
Ser Glu Tyr Leu Phe Arg His Ser Asp Asn Glu Leu Leu His Trp Met
                645                 650                 655
Val Ala Leu Asp Gly Lys Pro Leu Ala Ser Gly Glu Val Pro Leu Asp
                660                 665                 670
Val Ala Pro Gln Gly Lys Gln Leu Ile Glu Leu Pro Glu Leu Pro Gln
                675                 680                 685
Pro Glu Ser Ala Gly Gln Leu Trp Leu Thr Val Arg Val Val Gln Pro
                690                 695                 700
Asn Ala Thr Ala Trp Ser Glu Ala Gly His Ile Ser Ala Trp Gln Gln
705                 710                 715                 720
Trp Arg Leu Ala Glu Asn Leu Ser Val Thr Leu Pro Ala Ala Ser His
                725                 730                 735
Ala Ile Pro His Leu Thr Thr Ser Glu Met Asp Phe Cys Ile Glu Leu
                740                 745                 750
Gly Asn Lys Arg Trp Gln Phe Asn Arg Gln Ser Gly Phe Leu Ser Gln
                755                 760                 765
Met Trp Ile Gly Asp Lys Lys Gln Leu Leu Thr Pro Leu Arg Asp Gln
                770                 775                 780
Phe Thr Arg Ala Pro Leu Asp Asn Asp Ile Gly Val Ser Glu Ala Thr
785                 790                 795                 800
Arg Ile Asp Pro Asn Ala Trp Val Glu Arg Trp Lys Ala Ala Gly His
                805                 810                 815
Tyr Gln Ala Glu Ala Ala Leu Leu Gln Cys Thr Ala Asp Thr Leu Ala
                820                 825                 830
Asp Ala Val Leu Ile Thr Thr Ala His Ala Trp Gln His Gln Gly Lys
                835                 840                 845
Thr Leu Phe Ile Ser Arg Lys Thr Tyr Arg Ile Asp Gly Ser Gly Gln
850                 855                 860
Met Ala Ile Thr Val Asp Val Glu Val Ala Ser Asp Thr Pro His Pro
865                 870                 875                 880
Ala Arg Ile Gly Leu Asn Cys Gln Leu Ala Gln Val Ala Glu Arg Val
                885                 890                 895
Asn Trp Leu Gly Leu Gly Pro Gln Glu Asn Tyr Pro Asp Arg Leu Thr
                900                 905                 910
```

```
Ala Ala Cys Phe Asp Arg Trp Asp Leu Pro Leu Ser Asp Met Tyr Thr
        915                 920                 925
Pro Tyr Val Phe Pro Ser Glu Asn Gly Leu Arg Cys Gly Thr Arg Glu
    930                 935                 940
Leu Asn Tyr Gly Pro His Gln Trp Arg Gly Asp Phe Gln Phe Asn Ile
945                 950                 955                 960
Ser Arg Tyr Ser Gln Gln Gln Leu Met Glu Thr Ser His Arg His Leu
                965                 970                 975
Leu His Ala Glu Glu Gly Thr Trp Leu Asn Ile Asp Gly Phe His Met
            980                 985                 990
Gly Ile Gly Gly Asp Asp Ser Trp  Ser Pro Ser Val Ser  Ala Glu Phe
            995                 1000                1005
Gln Leu  Ser Ala Gly Arg Tyr  His Tyr Gln Leu Val  Trp Cys Gln
    1010                1015                    1020
Lys
```

<210> SEQ ID NO 3
<211> LENGTH: 1812
<212> TYPE: DNA
<213> ORGANISM: Escherichia coli

<400> SEQUENCE: 3

```
atgttacgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
aatcaggaag tgatggagca tcagggcggc tatacgccat tgaagccga tgtcacgccg     360
tatgttattg ccgggaaaag tgtacgtatc accgtttgtg tgaacaacga actgaactgg     420
cagactatcc cgccgggaat ggtgattacc gacgaaaacg caagaaaaa gcagtcttac     480
ttccatgatt tctttaacta tgccgggatc catcgcagcg taatgctcta caccacgccg     540
aacacctggg tggacgatat caccgtggtg acgcatgtcg cgcaagactg taaccacgcg     600
tctgttgact ggcaggtggt ggccaatggt gatgtcagcg ttgaactgcg tgatgcggat     660
caacaggtgg ttgcaactgg acaaggcact agcgggactt gcaagtggt gaatccgcac     720
ctctggcaac cggtgaagg ttatctctat gaactgtgcg tcacagccaa agccagaca     780
gagtgtgata tctacccgct tcgcgtcggc atccggtcag tggcagtgaa gggcgaacag     840
ttcctgatta ccacaaaacc gttctacttt actggctttg tcgtcatga agatgcggac     900
tgcgtggca aggattcga taacgtgctg atggtgcacg ccacgcatt aatggactgg     960
attgggccaa actcctaccg tacctcgcat taccttacg ctgaagagat gctcgactgg    1020
gcagatgaac atggcatcgt ggtgattgat gaaactgctg ctgtcggctt taacctctct    1080
ttaggcattg gtttcgaagc gggcaacaag ccgaaagaac tgtacagcga agaggcagtc    1140
aacggggaaa ctcagcaagc gcacttacag gcgattaaag agctgatagc gcgtgacaaa    1200
aaccacccaa gcgtggtgat gtggagtatt gccaacgaac cggatacccg tccgcaaggt    1260
gcacgggaat atttcgcgcc actggcggaa gcaacgcgta aactcgaccc gacgcgtccg    1320
atcacctgcg tcaatgtaat gttctgcgac gctcacaccg ataccatcag cgatctcttt    1380
gatgtgctgt gcctgaaccg ttattacgga tggtatgtcc aaagcggcga tttggaaacg    1440
```

```
gcagagaagg tactggaaaa agaacttctg gcctggcagg agaaactgca tcagccgatt      1500
atcatcaccg aatacggcgt ggatacgtta gccgggctgc actcaatgta caccgacatg      1560
tggagtgaag agtatcagtg tgcatggctg gatatgtatc accgcgtctt tgatcgcgtc      1620
agcgccgtcg tcggtgaaca ggtatggaat ttcgccgatt ttgcgacctc gcaaggcata      1680
ttgcgcgttg gcggtaacaa gaaagggatc ttcactcgcg accgcaaacc gaagtcggcg      1740
gcttttctgc tgcaaaaacg ctggactggc atgaacttcg gtgaaaaacc gcagcaggga      1800
ggcaaacaat ga                                                           1812
```

<210> SEQ ID NO 4
<211> LENGTH: 603
<212> TYPE: PRT
<213> ORGANISM: Escherichia coli

<400> SEQUENCE: 4

```
Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300
```

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
            325                 330                 335

Met Leu Asp Trp Ala Asp Glu His Gly Ile Val Val Ile Asp Glu Thr
        340                 345                 350

Ala Ala Val Gly Phe Asn Leu Ser Leu Gly Ile Gly Phe Glu Ala Gly
    355                 360                 365

Asn Lys Pro Lys Glu Leu Tyr Ser Glu Glu Ala Val Asn Gly Glu Thr
370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
            405                 410                 415

Arg Pro Gln Gly Ala Arg Glu Tyr Phe Ala Pro Leu Ala Glu Ala Thr
        420                 425                 430

Arg Lys Leu Asp Pro Thr Arg Pro Ile Thr Cys Val Asn Val Met Phe
    435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
            485                 490                 495

His Gln Pro Ile Ile Ile Thr Glu Tyr Gly Val Asp Thr Leu Ala Gly
        500                 505                 510

Leu His Ser Met Tyr Thr Asp Met Trp Ser Glu Glu Tyr Gln Cys Ala
    515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln Gly Ile
545                 550                 555                 560

Leu Arg Val Gly Gly Asn Lys Lys Gly Ile Phe Thr Arg Asp Arg Lys
            565                 570                 575

Pro Lys Ser Ala Ala Phe Leu Leu Gln Lys Arg Trp Thr Gly Met Asn
        580                 585                 590

Phe Gly Glu Lys Pro Gln Gln Gly Gly Lys Gln
    595                 600

<210> SEQ ID NO 5
<211> LENGTH: 2298
<212> TYPE: DNA
<213> ORGANISM: Escherichia coli

<400> SEQUENCE: 5
atgaaatggc tatgttcagt aggaatcgcg gtgagtctgg ccctacagcc agcactggcg      60
gatgatttat tcggcaacca tccattaacg cccgaagcgc gggatgcgtt cgtcaccgaa     120
ctgcttaaga aaatgacagt tgatgagaaa attggtcagc tgcgcttaat cagcgtcggc     180
ccggataacc cgaaagaggc gatccgcgag atgatcaaag acggtcaggt tggggcgatt     240
ttcaacaccg taacccgtca ggatatccgc gccatgcagg atcaggtgat ggaattaagc     300
cgcctgaaaa ttcctctttt ctttgcttac gacgtgctgc acggtcagcg cacggtgttc     360
ccgattagcc tcggtctggc ctcgtctttt aacctcgatg cagtgaaaac ggtcggacgt     420

```
gtctctgctt atgaagcggc agatgatggc ctgaatatga cctgggcacc gatggtcgat    480
gtctcgcgcg atccgcgctg gggacgtgct tccgaaggtt ttggcgaaga tacgtatctc    540
acctcaacaa tgggtaaaac catggtggaa gcgatgcagg gtaaaagccc ggcagatcgc    600
tactcggtga tgaccagcgt caaacacttt gccgcatacg gcgcggtaga aggcggtaaa    660
gagtacaaca ccgtcgatat gagtccgcag cgcctgttta atgattatat gccgccgtac    720
aaagcggggc tggacgcagg cagcggcgcg gtgatggtgg cgctgaactc gctgaacggc    780
acgccagcca cctccgattc ctggctgctg aaagatgttc tgcgcgacca gtgggctttt    840
aaaggcatca ccgtttccga tcacggtgca atcaaagagc tgattaaaca tggcacggcg    900
gcagacccgg aagatgcggt gcgcgtggcg ctgaaatccg aatcaacat gagcatgagc    960
gacgagtact actcgaagta tctgcctggg ttgattaaat ccggcaaagt gacgatggca   1020
gagctggacg atgctgcccg ccatgtactg aacgttaaat atgatatggg gttgtttaac   1080
gacccataca gccatttggg gccgaaagag tctgacccgg tggataccaa tgccgaaagc   1140
cgcctgcacc gtaaagaagc gcgtgaagtg gcgcgcgaaa gcttggtgtt gctgaaaaac   1200
cgtctcgaaa cgttaccgct gaaaaaatcg gccaccattg cggtggttgg ccactggcg    1260
gacagtaaac gtgacgtgat gggcagctgg tccgcagccg tgttgccga tcaatccgtg    1320
accgtactga ccgggattaa aaatgccgtc ggtgaaaacg gtaaagtgct gtatgccaaa   1380
ggggcgaacg ttaccagtga caaaggcatt atcgatttcc tgaatcagta tgaagaagcg   1440
gtcaaagtcg atccgcgttc gccgcaagag atgattgatg aagcggtgca gacggcgaaa   1500
caatctgatg tggtggtggc tgtagtcggt gaagcacagg ggatggcgca cgaagcctcc   1560
agccggaccg atatcactat tccgcaaagc caacgtgact tgattgcggc gctgaaagcc   1620
accggtaaac cgctggtgct ggtgctgatg aacgggcgtc cgctggcgct ggtgaaagaa   1680
gatcagcagg ctgatgcgat tctggaaacc tggtttgcgg ggactgaagg cggtaatgca   1740
attgccgatg tattgtttgg cgattacaac ccgtccggca agctgccaat gtccttcccg   1800
cgttctgtcg ggcagatccc ggtgtactac agccatctga ataccggtcg cccgtataat   1860
gccgacaagc cgaacaaata cacttcgcgt tattttgatg aagctaacgg ggcgttgtat   1920
ccgttcggct atgggctgag ctacaccact ttcaccgtct ctgatgtgaa actttctgcg   1980
ccgaccatga agcgtgacgg caaagtgact gccagcgtgc aggtgacgaa caccggtaag   2040
cgcgagggtg ccacggtagt gcagatgtac ttgcaggatg tgacggcttc catgagtcgc   2100
cctgtgaaac agctgaaagg ctttgagaaa atcaccctga accgggcga aactcagact   2160
gtcagcttcc cgatcgatat tgaggcgctg aagttctgga atcaacagat gaaatatgac   2220
gccgagcctg gcaagttcaa tgtctttatc ggcactgatt ccgcacgcgt taagaaaggc   2280
gagtttgagt tgctgtaa                                                 2298
```

<210> SEQ ID NO 6
<211> LENGTH: 765
<212> TYPE: PRT
<213> ORGANISM: Escherichia coli

<400> SEQUENCE: 6

Met Lys Trp Leu Cys Ser Val Gly Ile Ala Val Ser Leu Ala Leu Gln
1               5                   10                  15

Pro Ala Leu Ala Asp Asp Leu Phe Gly Asn His Pro Leu Thr Pro Glu
            20                  25                  30

```
Ala Arg Asp Ala Phe Val Thr Glu Leu Leu Lys Lys Met Thr Val Asp
         35                  40                  45

Glu Lys Ile Gly Gln Leu Arg Leu Ile Ser Val Gly Pro Asp Asn Pro
 50                  55                  60

Lys Glu Ala Ile Arg Glu Met Ile Lys Asp Gly Gln Val Gly Ala Ile
 65                  70                  75                  80

Phe Asn Thr Val Thr Arg Gln Asp Ile Arg Ala Met Gln Asp Gln Val
                 85                  90                  95

Met Glu Leu Ser Arg Leu Lys Ile Pro Leu Phe Ala Tyr Asp Val
                100                 105                 110

Leu His Gly Gln Arg Thr Val Phe Pro Ile Ser Leu Gly Leu Ala Ser
         115                 120                 125

Ser Phe Asn Leu Asp Ala Val Lys Thr Val Gly Arg Val Ser Ala Tyr
     130                 135                 140

Glu Ala Ala Asp Asp Gly Leu Asn Met Thr Trp Ala Pro Met Val Asp
145                 150                 155                 160

Val Ser Arg Asp Pro Arg Trp Gly Arg Ala Ser Glu Gly Phe Gly Glu
                165                 170                 175

Asp Thr Tyr Leu Thr Ser Thr Met Gly Lys Thr Met Val Glu Ala Met
                180                 185                 190

Gln Gly Lys Ser Pro Ala Asp Arg Tyr Ser Val Met Thr Ser Val Lys
         195                 200                 205

His Phe Ala Ala Tyr Gly Ala Val Glu Gly Gly Lys Glu Tyr Asn Thr
     210                 215                 220

Val Asp Met Ser Pro Gln Arg Leu Phe Asn Asp Tyr Met Pro Pro Tyr
225                 230                 235                 240

Lys Ala Gly Leu Asp Ala Gly Ser Gly Ala Val Met Val Ala Leu Asn
                245                 250                 255

Ser Leu Asn Gly Thr Pro Ala Thr Ser Asp Ser Trp Leu Leu Lys Asp
                260                 265                 270

Val Leu Arg Asp Gln Trp Gly Phe Lys Gly Ile Thr Val Ser Asp His
         275                 280                 285

Gly Ala Ile Lys Glu Leu Ile Lys His Gly Thr Ala Ala Asp Pro Glu
     290                 295                 300

Asp Ala Val Arg Val Ala Leu Lys Ser Gly Ile Asn Met Ser Met Ser
305                 310                 315                 320

Asp Glu Tyr Tyr Ser Lys Tyr Leu Pro Gly Leu Ile Lys Ser Gly Lys
                325                 330                 335

Val Thr Met Ala Glu Leu Asp Asp Ala Ala Arg His Val Leu Asn Val
         340                 345                 350

Lys Tyr Asp Met Gly Leu Phe Asn Asp Pro Tyr Ser His Leu Gly Pro
     355                 360                 365

Lys Glu Ser Asp Pro Val Asp Thr Asn Ala Glu Ser Arg Leu His Arg
370                 375                 380

Lys Glu Ala Arg Glu Val Ala Arg Glu Ser Leu Val Leu Leu Lys Asn
385                 390                 395                 400

Arg Leu Glu Thr Leu Pro Leu Lys Lys Ser Ala Thr Ile Ala Val Val
                405                 410                 415

Gly Pro Leu Ala Asp Ser Lys Arg Asp Val Met Gly Ser Trp Ser Ala
                420                 425                 430

Ala Gly Val Ala Asp Gln Ser Val Thr Val Leu Thr Gly Ile Lys Asn
         435                 440                 445

Ala Val Gly Glu Asn Gly Lys Val Leu Tyr Ala Lys Gly Ala Asn Val
```

|  |  |  | 450 |  |  |  |  | 455 |  |  |  |  | 460 |  |  |
|---|---|---|---|---|---|---|---|---|---|---|---|---|---|---|---|
| Thr | Ser | Asp | Lys | Gly | Ile | Ile | Asp | Phe | Leu | Asn | Gln | Tyr | Glu | Glu | Ala |
| 465 |  |  |  |  | 470 |  |  |  |  | 475 |  |  |  |  | 480 |
| Val | Lys | Val | Asp | Pro | Arg | Ser | Pro | Gln | Glu | Met | Ile | Asp | Glu | Ala | Val |
|  |  |  |  | 485 |  |  |  |  | 490 |  |  |  |  | 495 |  |
| Gln | Thr | Ala | Lys | Gln | Ser | Asp | Val | Val | Ala | Val | Val | Gly | Glu | Ala |  |
|  |  |  | 500 |  |  |  |  | 505 |  |  |  |  | 510 |  |  |
| Gln | Gly | Met | Ala | His | Glu | Ala | Ser | Ser | Arg | Thr | Asp | Ile | Thr | Ile | Pro |
|  |  | 515 |  |  |  |  | 520 |  |  |  |  | 525 |  |  |  |
| Gln | Ser | Gln | Arg | Asp | Leu | Ile | Ala | Ala | Leu | Lys | Ala | Thr | Gly | Lys | Pro |
|  | 530 |  |  |  |  | 535 |  |  |  |  | 540 |  |  |  |  |
| Leu | Val | Leu | Val | Leu | Met | Asn | Gly | Arg | Pro | Leu | Ala | Leu | Val | Lys | Glu |
| 545 |  |  |  |  | 550 |  |  |  |  | 555 |  |  |  |  | 560 |
| Asp | Gln | Gln | Ala | Asp | Ala | Ile | Leu | Glu | Thr | Trp | Phe | Ala | Gly | Thr | Glu |
|  |  |  |  | 565 |  |  |  |  | 570 |  |  |  |  | 575 |  |
| Gly | Gly | Asn | Ala | Ile | Ala | Asp | Val | Leu | Phe | Gly | Asp | Tyr | Asn | Pro | Ser |
|  |  |  | 580 |  |  |  |  | 585 |  |  |  |  | 590 |  |  |
| Gly | Lys | Leu | Pro | Met | Ser | Phe | Pro | Arg | Ser | Val | Gly | Gln | Ile | Pro | Val |
|  |  | 595 |  |  |  |  | 600 |  |  |  |  | 605 |  |  |  |
| Tyr | Tyr | Ser | His | Leu | Asn | Thr | Gly | Arg | Pro | Tyr | Asn | Ala | Asp | Lys | Pro |
|  | 610 |  |  |  |  | 615 |  |  |  |  | 620 |  |  |  |  |
| Asn | Lys | Tyr | Thr | Ser | Arg | Tyr | Phe | Asp | Glu | Ala | Asn | Gly | Ala | Leu | Tyr |
| 625 |  |  |  |  | 630 |  |  |  |  | 635 |  |  |  |  | 640 |
| Pro | Phe | Gly | Tyr | Gly | Leu | Ser | Tyr | Thr | Thr | Phe | Thr | Val | Ser | Asp | Val |
|  |  |  |  | 645 |  |  |  |  | 650 |  |  |  |  | 655 |  |
| Lys | Leu | Ser | Ala | Pro | Thr | Met | Lys | Arg | Asp | Gly | Lys | Val | Thr | Ala | Ser |
|  |  |  | 660 |  |  |  |  | 665 |  |  |  |  | 670 |  |  |
| Val | Gln | Val | Thr | Asn | Thr | Gly | Lys | Arg | Glu | Gly | Ala | Thr | Val | Val | Gln |
|  |  |  |  | 675 |  |  |  |  | 680 |  |  |  |  | 685 |  |
| Met | Tyr | Leu | Gln | Asp | Val | Thr | Ala | Ser | Met | Ser | Arg | Pro | Val | Lys | Gln |
|  | 690 |  |  |  |  | 695 |  |  |  |  | 700 |  |  |  |  |
| Leu | Lys | Gly | Phe | Glu | Lys | Ile | Thr | Leu | Lys | Pro | Gly | Glu | Thr | Gln | Thr |
| 705 |  |  |  |  | 710 |  |  |  |  | 715 |  |  |  |  | 720 |
| Val | Ser | Phe | Pro | Ile | Asp | Ile | Glu | Ala | Leu | Lys | Phe | Trp | Asn | Gln | Gln |
|  |  |  |  | 725 |  |  |  |  | 730 |  |  |  |  | 735 |  |
| Met | Lys | Tyr | Asp | Ala | Glu | Pro | Gly | Lys | Phe | Asn | Val | Phe | Ile | Gly | Thr |
|  |  |  | 740 |  |  |  |  | 745 |  |  |  |  | 750 |  |  |
| Asp | Ser | Ala | Arg | Val | Lys | Lys | Gly | Glu | Phe | Glu | Leu | Leu |  |  |  |
|  |  |  | 755 |  |  |  |  | 760 |  |  |  |  | 765 |  |  |

<210> SEQ ID NO 7
<211> LENGTH: 200
<212> TYPE: DNA
<213> ORGANISM: Escherichia coli

<400> SEQUENCE: 7
caatacgcaa accgcctctc cccgcgcgtt ggccgattca ttaatgcagc tggcacgaca    60
ggtttcccga ctggaaagcg ggcagtgagc gcaacgcaat taatgtgagt tagctcactc   120
attaggcacc ccaggcttta cactttatgc ttccggctcg tatgttgtgt ggaattgtga   180
gcggataaca atttcacaca                                              200

<210> SEQ ID NO 8
<211> LENGTH: 240
<212> TYPE: DNA

<213> ORGANISM: Escherichia coli

<400> SEQUENCE: 8

| | | | | |
|---|---|---|---|---|
| cggcgaaata gtaatcacga ggtcaggttc ttaccttaaa ttttcgacgg aaaaccacgt | | | | 60 |
| aaaaaacgtc gattttcaa gatacagcgt gaatttcag gaaatgcggt gagcatcaca | | | | 120 |
| tcaccacaat tcagcaaatt gtgaacatca tcacgttcat cttcccctgg ttgccaatgg | | | | 180 |
| cccatttcc tgtcagtaac gagaaggtcg cgagttcagg cgcttttag actggtcgta | | | | 240 |

<210> SEQ ID NO 9
<211> LENGTH: 54
<212> TYPE: DNA
<213> ORGANISM: Escherichia coli

<400> SEQUENCE: 9
tccctatcag tgatagagat tgacatccct atcagtgata gagatactga gcac    54

<210> SEQ ID NO 10
<211> LENGTH: 49
<212> TYPE: DNA
<213> ORGANISM: Escherichia coli

<400> SEQUENCE: 10
taacaccgtg cgtgttgact attttacctc tggcggtgat aatggttgc    49

<210> SEQ ID NO 11
<211> LENGTH: 157
<212> TYPE: DNA
<213> ORGANISM: Pseudomonas aeruginosa

<400> SEQUENCE: 11

| | |
|---|---|
| gcccctcgct gagcgcgtcc cggagctggg ggcaacctag ctgccacctg cttttctgct | 60 |
| agctattcca gcgaaaacat acagatttcc ggcgaaatca aggctacctg ccagttctgg | 120 |
| caggtttggc cgcgggttct ttttggtaca cgaaagc | 157 |

<210> SEQ ID NO 12
<211> LENGTH: 55
<212> TYPE: DNA
<213> ORGANISM: Vibrio fischeri

<400> SEQUENCE: 12
acctgtagga tcgtacaggt ttacgcaaga aaatggtttg ttatagtcga ataaa    55

<210> SEQ ID NO 13
<211> LENGTH: 95
<212> TYPE: DNA
<213> ORGANISM: Escherichia coli

<400> SEQUENCE: 13

| | |
|---|---|
| cccttccaga attcgataaa tctctggttt attgtgcagt ttatggttcc aaaatcgcct | 60 |
| tttgctgtat atactcacag cataactgta tatac | 95 |

<210> SEQ ID NO 14
<211> LENGTH: 1203
<212> TYPE: DNA
<213> ORGANISM: Escherichia coli

<400> SEQUENCE: 14

| | |
|---|---|
| ttatgacaac ttgacggcta catcattcac ttttcttca caaccggcac gaaactcgct | 60 |
| cgggctggcc ccgtgcatt ttttaaatac tcgcgagaaa tagagttgat cgtcaaaacc | 120 |

```
aacattgcga ccgacggtgg cgataggcat ccgggtagtg ctcaaaagca gcttcgcctg    180
actaatgcgt tggtcctcgc gccagcttaa gacgctaatc cctaactgct ggcggaaaag    240
atgtgacaga cgcgacggcg acaagcaaac atgctgtgcg acgctggcga tatcaaaatt    300
gctgtctgcc aggtgatcgc tgatgtactg acaagcctcg cgtacccgat tatccatcgg    360
tggatggagc gactcgttaa tcgcttccat gcgccgcagt aacaattgct caagcagatt    420
tatcgccagc agctccgaat agcgcccttc cccttgcccg gcgttaatga tttgcccaaa    480
caggtcgctg aaatgcggct ggtgcgcttc atccgggcga agaaacccg tattggcaaa     540 tattgacggc cagttaagcc attcatgcca gtaggcgcgc ggacgaaagt aaacccactg    600
gtgataccat cgcgagcct ccggatgacg accgtagtga tgaatctctc ctggcgggaa     660
cagcaaaata tcacccggtc ggcagacaaa ttctcgtccc tgattttttca ccaccccctg    720 accgcgaatg gtgagattga aatataacc tttcattccc agcggtcggt cgataaaaaa     780
atcgagataa ccgttggcct caatcggcgt taaacccgcc accagatggg cgttaaacga    840
gtatcccggc agcaggggat catttttgcgc ttcagccata cttttcatac tcccaccatt    900
cagagaagaa accaattgtc catattgcat cagacattgc cgtcactgcg tcttttactg    960
gctcttctcg ctaacccaac cggtaacccc gcttattaaa agcattctgt aacaaagcgg   1020
gaccaaagcc atgacaaaaa cgcgtaacaa aagtgtctat aatcacggca gaaaagtcca   1080
cattgattat ttgcacggcg tcacactttg ctatgccata gcatttttat ccataagatt   1140
agcggatcct acctgacgct ttttatcgca actctctact gtttctccat acccgttttt   1200
ttg                                                                 1203

<210> SEQ ID NO 15
<211> LENGTH: 103
<212> TYPE: DNA
<213> ORGANISM: Artificial Sequence
<220> FEATURE:
<223> OTHER INFORMATION: Mycobacterium avium paratuberculosis

<400> SEQUENCE: 15
tacgcggtac tggataaaca tttcaccact gtaaggaaaa taattcttat ttcgattgtc     60 cttttttaccc ttctcgttcg actcatagct gaacacaaca aaa                    103

<210> SEQ ID NO 16
<211> LENGTH: 22
<212> TYPE: DNA
<213> ORGANISM: Escherichia coli

<400> SEQUENCE: 16
aaaatgacaa ttttgtcatt tt                                             22

<210> SEQ ID NO 17
<211> LENGTH: 23
<212> TYPE: DNA
<213> ORGANISM: Artificial Sequence
<220> FEATURE:
<223> OTHER INFORMATION: T7 Bacteriophage

<400> SEQUENCE: 17
taatacgact cactataggg aga                                            23

<210> SEQ ID NO 18
<211> LENGTH: 405
<212> TYPE: DNA
```

```
<213> ORGANISM: Escherichia coli

<400> SEQUENCE: 18
cactgaagtg atcctcgcca ccaaccccac ggttgaaggt gaagctaccg ctaactacat    60
tgccgagctt tgcgcgcaat atgacgtgga agccagccga atcgctcatg gcgttccggt   120
tggcggcgag ctggaaatgg tcgacggcac cacgttgtca cactcccttg ccgggcgtca   180
taagattcgt ttttaagcaa acgagagcag gatcacctgc tctcgcttga aattattctc   240
ccttgtcccc atctctccca catcctgttt ttaaccttaa aatggcatta ttgaggtaga   300
cctacatgaa aggacaagaa actcgtggtt ttcagtcaga agtgaaacag cttctgcacc   360
tgatgatcca ttctctctat tccaataaag aaatcttcct gcgtg                   405

<210> SEQ ID NO 19
<211> LENGTH: 35
<212> TYPE: DNA
<213> ORGANISM: Escherichia coli

<400> SEQUENCE: 19
ttgacggcta gctcagtcct aggtacagtg ctagc                               35

<210> SEQ ID NO 20
<211> LENGTH: 240
<212> TYPE: DNA
<213> ORGANISM: Artificial Sequence
<220> FEATURE:
<223> OTHER INFORMATION: E. coli rhamnose promoter (pRha)

<400> SEQUENCE: 20
cggcgaaata gtaatcacga ggtcaggttc ttaccttaaa ttttcgacgg aaaaccacgt    60
aaaaaacgtc gatttttcaa gatacagcgt gaatttttcag gaaatgcggt gagcatcaca   120
tcaccacaat tcagcaaatt gtgaacatca tcacgttcat cttccctgg ttgccaatgg    180 cccatttttcc tgtcagtaac gagaaggtcg cgagttcagg cgcttttag actggtcgta   240

<210> SEQ ID NO 21
<211> LENGTH: 76
<212> TYPE: DNA
<213> ORGANISM: Artificial Sequence
<220> FEATURE:
<223> OTHER INFORMATION: Thiobacillus ferrioxidans

<400> SEQUENCE: 21
ggcaggaaga ccgggcgcat gagcgtattt tgtttatcta atatgcctga aagcgcatac    60
cgctatggag ggggtt                                                    76
```